(12) United States Patent
Revilla et al.

(10) Patent No.: US 10,214,772 B2
(45) Date of Patent: Feb. 26, 2019

(54) TEST CARD FOR ASSAY AND METHOD OF MANUFACTURING SAME

(71) Applicant: FluxErgy, LLC, Irvine, CA (US)

(72) Inventors: Ryan Alan Revilla, Downey, CA (US); Roy James Heltsley, Foothill Ranch, CA (US); Steve Hoe Lee, Glendale, CA (US); Tej Rushikesh Patel, Aliso Viejo, CA (US)

(73) Assignee: FluxErgy, LLC, Irvine, CA (US)

( * ) Notice: Subject to any disclaimer, the term of this patent is extended or adjusted under 35 U.S.C. 154(b) by 109 days.

(21) Appl. No.: 15/185,661

(22) Filed: Jun. 17, 2016

(65) Prior Publication Data
US 2016/0369323 A1   Dec. 22, 2016

Related U.S. Application Data

(60) Provisional application No. 62/182,992, filed on Jun. 22, 2015, provisional application No. 62/187,471, filed on Jul. 1, 2015.

(51) Int. Cl.
*C12Q 1/686* (2018.01)
*B01L 3/00* (2006.01)
*B01L 7/00* (2006.01)

(52) U.S. Cl.
CPC .......... *C12Q 1/686* (2013.01); *B01L 3/5027* (2013.01); *B01L 7/52* (2013.01); *B01L 2200/04* (2013.01);
(Continued)

(58) Field of Classification Search
CPC ..... B01L 2300/0816; B01L 2300/0645; B01L 2300/1827; B01L 7/525; B01L 2300/1822;
(Continued)

(56) References Cited

U.S. PATENT DOCUMENTS 5,147,606 A * 9/1992 Charlton ............ B01L 3/502753
422/412
5,229,297 A   7/1993 Schnipelsky et al.
(Continued)

FOREIGN PATENT DOCUMENTS

WO   1993022054   11/1993
WO   2014055963   4/2014

OTHER PUBLICATIONS

Gubala et al. (Anal chem 2012, 84 (2), pp. 487-515) Pub date Dec. 21, 2011 (Year: 2011).*
(Continued)

*Primary Examiner* — Sally A Merkling
(74) *Attorney, Agent, or Firm* — K&L Gates LLP; Louis C. Cullman; Joseph F. Arand

(57) ABSTRACT

A disposable test card configured to accept a fluid sample for an assay, and a method of manufacturing same, is disclosed herein. In a general example embodiment, a test card for analyzing a fluid sample includes a first substrate layer including an inlet port and an outlet port, a channel layer bonded to the first substrate layer, the channel layer including a microchannel placing the inlet port in fluid communication with the outlet port, and a second substrate layer bonded to the channel layer, the second substrate layer having electrodes printed adjacent to a target zone of the microchannel of the channel layer, wherein the electrodes are configured to raise the temperature of the fluid sample within the target zone of the microchannel when a current is applied thereto.

17 Claims, 16 Drawing Sheets

(52) U.S. Cl.
CPC ............... B01L 2200/0684 (2013.01); B01L 2200/0689 (2013.01); B01L 2300/0816 (2013.01); B01L 2300/0867 (2013.01); B01L 2300/0887 (2013.01); B01L 2300/161 (2013.01); B01L 2400/049 (2013.01)

(58) Field of Classification Search
CPC ..... B01L 7/00; C12Q 1/686; C12Q 2565/629; C12Q 1/04; G01N 33/5091; G01N 33/569; B01J 2219/00722; B01J 19/0093; B01J 2219/00873; C12M 23/16; F16K 2099/0084; F16K 2099/0074; F16K 2099/008
See application file for complete search history.

(56) References Cited

U.S. PATENT DOCUMENTS

| | | | |
|---|---|---|---|
| 5,726,026 A * | 3/1998 | Wilding | B01D 67/0062 366/DIG. 3 |
| 5,976,336 A | 11/1999 | Dubrow et al. | |
| 6,068,752 A | 5/2000 | Dubrow et al. | |
| 6,071,478 A | 6/2000 | Chow | |
| 6,153,073 A | 11/2000 | Dubrow et al. | |
| 6,235,175 B1 | 5/2001 | Dubrow et al. | |
| 6,303,343 B1 | 10/2001 | Kopf-Sill | |
| 6,399,025 B1 | 6/2002 | Chow | |
| 6,428,987 B2 | 8/2002 | Franzen | |
| 6,437,551 B1 | 8/2002 | Krulevitch et al. | |
| 6,576,459 B2 | 6/2003 | Miles et al. | |
| 7,033,474 B1 | 4/2006 | Dubrow et al. | |
| 7,309,467 B2 | 12/2007 | Chen et al. | |
| 7,431,888 B2 | 10/2008 | Frechet et al. | |
| 7,678,336 B2 | 3/2010 | Chang et al. | |
| 7,811,523 B2 | 10/2010 | Bjorneson | |
| 7,867,754 B1 | 1/2011 | Regnier et al. | |
| 7,883,669 B2 | 2/2011 | Sun et al. | |
| 7,915,030 B2 | 3/2011 | Inoue et al. | |
| 7,919,062 B2 | 4/2011 | Yuen | |
| 7,981,237 B2 | 7/2011 | Park et al. | |
| 8,053,239 B2 | 11/2011 | Wheeler et al. | |
| 8,158,926 B2 | 4/2012 | Feng et al. | |
| 8,202,491 B2 | 6/2012 | Masters et al. | |
| 8,216,827 B2 | 7/2012 | Pouteau et al. | |
| 8,247,176 B2 | 8/2012 | Pourahmadi et al. | |
| 8,289,519 B2 | 10/2012 | Zare et al. | |
| 8,343,778 B2 | 1/2013 | Yu et al. | |
| 8,349,276 B2 | 1/2013 | Pamula et al. | |
| 8,367,021 B2 | 2/2013 | Kennedy et al. | |
| 8,394,341 B2 | 3/2013 | Reinhardt et al. | |
| 8,409,848 B2 | 4/2013 | Zeng et al. | |
| 8,540,946 B2 | 9/2013 | Padmanabhan et al. | |
| 8,557,199 B2 | 10/2013 | Heath et al. | |
| 8,557,518 B2 | 10/2013 | Jovanovich et al. | |
| 8,562,918 B2 | 10/2013 | Jovanovich et al. | |
| 8,592,157 B2 | 11/2013 | Pourahmadi et al. | |
| 8,597,574 B2 | 12/2013 | Gumbrecht et al. | |
| 8,603,414 B2 | 12/2013 | Omuro et al. | |
| 8,790,595 B2 | 7/2014 | Polwart et al. | |
| 8,852,527 B2 | 10/2014 | Thomas et al. | |
| 8,874,273 B2 | 10/2014 | Sun et al. | |
| 8,894,946 B2 | 11/2014 | Nielsen et al. | |
| 8,911,636 B2 | 12/2014 | Gautham | |
| 8,911,989 B2 | 12/2014 | Lee et al. | |
| 8,936,762 B2 | 1/2015 | Ehrlich et al. | |
| 8,940,147 B1 | 1/2015 | Bartsch et al. | |
| 8,962,252 B2 | 2/2015 | Liang et al. | |
| 9,017,946 B2 | 4/2015 | Hasson | |
| 9,114,398 B2 | 8/2015 | Knight et al. | |
| 9,138,744 B2 | 9/2015 | Tsao et al. | |
| 9,170,138 B2 | 10/2015 | Giovangrandi et al. | |
| 9,328,344 B2 | 5/2016 | Link et al. | |
| 9,335,247 B2 | 5/2016 | Sharpe et al. | |
| 9,364,833 B2 | 6/2016 | Bergstedt | |
| 9,540,686 B2 | 1/2017 | Zeng et al. | |
| 2003/0155344 A1 | 8/2003 | Cobb | |
| 2004/0193202 A1 | 9/2004 | Allen | |
| 2005/0196779 A1 | 9/2005 | Ho et al. | |
| 2005/0233440 A1 | 10/2005 | Scurati et al. | |
| 2006/0094028 A1 | 5/2006 | Danna et al. | |
| 2007/0015179 A1 | 1/2007 | Klapperich et al. | |
| 2007/0154895 A1 | 7/2007 | Spaid et al. | |
| 2007/0163175 A1 * | 7/2007 | Kihara | B01J 19/0093 48/61 |
| 2007/0190828 A1 | 8/2007 | Goldman et al. | |
| 2008/0241910 A1 | 10/2008 | Jung et al. | |
| 2008/0253633 A1 | 10/2008 | Xia et al. | |
| 2009/0053726 A1 | 2/2009 | Owen et al. | |
| 2009/0140170 A1 | 6/2009 | Nevill et al. | |
| 2009/0143233 A1 | 6/2009 | Knight et al. | |
| 2009/0186404 A1 * | 7/2009 | Kim | B01L 3/5027 435/303.1 |
| 2009/0215157 A1 | 8/2009 | Jung et al. | |
| 2009/0215194 A1 | 8/2009 | Magni et al. | |
| 2009/0311717 A1 | 12/2009 | De Sonneville et al. | |
| 2010/0203521 A1 | 8/2010 | Klapperich et al. | |
| 2010/0261286 A1 * | 10/2010 | Kim | B01L 3/502707 436/149 |
| 2010/0291584 A1 | 11/2010 | Tseng et al. | |
| 2011/0039280 A1 | 2/2011 | Leary et al. | |
| 2011/0206545 A1 | 8/2011 | Junod et al. | |
| 2011/0269131 A1 | 11/2011 | Chiu et al. | |
| 2011/0301535 A1 | 12/2011 | Takayama et al. | |
| 2011/0315559 A1 | 12/2011 | Holt et al. | |
| 2012/0140055 A1 | 6/2012 | Narusawa et al. | |
| 2012/0145253 A1 | 6/2012 | Zeng et al. | |
| 2012/0195810 A1 | 8/2012 | Cohen et al. | |
| 2012/0244043 A1 | 9/2012 | LeBlanc et al. | |
| 2012/0244604 A1 | 9/2012 | Kornilovich | |
| 2012/0283108 A1 | 11/2012 | Sampas | |
| 2012/0309010 A1 | 12/2012 | Shuber | |
| 2013/0052725 A1 | 2/2013 | Yazdanfar | |
| 2013/0149215 A1 | 6/2013 | Dekker et al. | |
| 2013/0224781 A1 | 8/2013 | Jung et al. | |
| 2013/0244906 A1 | 8/2013 | Collins | |
| 2013/0236907 A1 | 9/2013 | Petersen et al. | |
| 2013/0345096 A1 | 12/2013 | Wan | |
| 2014/0038191 A1 | 2/2014 | Liang et al. | |
| 2014/0141424 A1 | 5/2014 | Pourahmadi et al. | |
| 2014/0161686 A1 | 6/2014 | Bort et al. | |
| 2014/0199764 A1 | 7/2014 | Domansky | |
| 2014/0200154 A1 | 7/2014 | Sugarman et al. | |
| 2014/0248621 A1 | 9/2014 | Collins | |
| 2014/0295441 A1 | 10/2014 | Egan et al. | |
| 2014/0307931 A1 | 10/2014 | Gierahn et al. | |
| 2014/0309508 A1 | 10/2014 | Kim et al. | |
| 2015/0024426 A1 | 1/2015 | De Oliveira Garcia Da Fonseca et al. | |
| 2015/0125947 A1 | 5/2015 | Korczyk et al. | |
| 2015/0238967 A1 | 8/2015 | Erickson et al. | |
| 2015/0290644 A1 | 10/2015 | Prentice et al. | |
| 2016/0033311 A1 | 2/2016 | Giovangrandi et al. | |
| 2016/0069913 A1 | 3/2016 | Bakhru et al. | |
| 2016/0144358 A1 | 5/2016 | Patel | |
| 2016/0296933 A1 | 10/2016 | Chiou et al. | |
| 2016/0334351 A1 | 11/2016 | Lu et al. | |
| 2016/0340716 A1 | 11/2016 | Ortac et al. | |
| 2017/0001196 A1 | 1/2017 | Zhang et al. | |
| 2017/0008009 A1 | 1/2017 | Azpiroz et al. | |
| 2017/0021354 A1 | 1/2017 | Kim et al. | |
| 2017/0058324 A1 | 3/2017 | Balog et al. | |

OTHER PUBLICATIONS

Creative Materials Product Description—Dielectric inks and coatings offerings (Year: 2015).*

International Preliminary Report on Patentability issued in related International Patent Application No. PCT/US2016/038152 dated Jun. 28, 2017.

Miralles et al., "A Review of Heating Temperature Control in Microfluidic Systems: Techniques and Applications," Diagnostics, 2013, No. 3, pp. 33-67.

(56) References Cited

OTHER PUBLICATIONS

Wang et al., "A miniaturized quantitative polymerase chain reaction system for DNA amplification and detection." Sensors and Actuators, No. B 141, 2009, pp. 329-337.
Hsieh et al., "Enhancement of thermal uniformity for a microthermal cycler and its applicaiton for polymerase chain reaction," Sensors and Actuators, B 130 (2008), pp. 848-856.
International Preliminary Report on Patentability issued in related International Patent Application No. PCT/US2016/038124 dated Jun. 26, 2017.
International Preliminary Report on Patentability issued in related International Patent Application No. PCT/US2016/038157 dated Jun. 19, 2017.
International Search Report and Written Opinion issued in related International Patent Application No. PCT/US2016/038152 dated Sep. 14, 2016. 12 pages.
International Search Report and Written Opinion issued in related International Patent Application No. PCT/US2016/038124 dated Sep. 8, 2016. 12 pages.
International Search Report and Written Opinion issued in related International Patent Application No. PCT/US2016/038157 dated Oct. 28, 2016. 12 pages.

\* cited by examiner

TEST CARD FOR ASSAY AND METHOD OF MANUFACTURING SAME

PRIORITY CLAIM AND CROSS-REFERENCE TO RELATED APPLICATIONS

This application claims priority to U.S. Provisional Patent Application No. 62/182,992, entitled "Point-Of-Care PCR Assay for Infectious Agents", filed Jun. 22, 2015, and U.S. Provisional Patent Application No. 62/187,471, entitled "Point-Of-Care PCR Assay for Infectious Agents", filed Jul. 1, 2015, the entire contents of each of which are hereby incorporated by reference and relied upon. This application is also related to U.S. application Ser. No. 15/185,640, entitled "Device for Analyzing a Fluid Sample and Use of Test Card with Same", and U.S. application Ser. No. 15/185,714, entitled "Camera Imaging System for a Fluid Sample Assay and Method of Using Same", the entire contents of each of which are hereby incorporated by reference and relied upon.

FIELD OF THE DISCLOSURE

The present disclosure relates generally to a test card configured to accept a fluid sample for an assay, and more specifically to a non-expensive, disposable test card and a method of manufacturing same.

BACKGROUND OF THE DISCLOSURE

Point-of-care (POC) in vitro diagnostics tests (IVDT) have traditionally had two major categories, nucleic acid amplification tests (NAAT) or immunoassay-based tests. The former directly detects the pathogen's DNA or RNA, while the latter detects antibodies or antigens generated by the immune system response to the pathogen.

Current POC diagnostic immunoassays lack the high sensitivity and specificity of nucleic acid amplification methods. This becomes more pronounced during the initial stages of infection, often within 168 hours. Taking the case of Dengue virus in whole blood, immunoglobulin M (IgM) and immunoglobulin G (IgG) remain undetectable in the majority of patients until 5 and 10 days post-infection, respectively, whereas nucleic acid can be found as early as 0 to 7 days. Moreover, many immunoassay tests are unable to detect infectious agents until 3 months after the initial onset of the infection. This delay is due to the time it takes for the body's immune system to respond to an infection.

POC diagnostic assays developed utilizing NAATs have very high sensitivities and specificities, matching those of currently accepted laboratory tests. The primary mechanism of NAAT based systems is to directly detect an infectious agent's nucleic acid, lending to the test's ability to detect diseases within the first few days of the onset of infection. In addition, by careful primer design, NAATs also have the ability to have very high specificity and sensitivity compared to immunoassay based testing. The largest drawback of NAATs compared to immunoassay-based tests is the complicated equipment and/or processes required to prepare a sample for testing.

SUMMARY OF THE DISCLOSURE

Described herein is a disposable test card configured to accept a fluid sample for an assay and a method of manufacturing same. In a general example embodiment, a test card for analysing a fluid sample includes a first substrate layer including an inlet port and an outlet port, a channel layer bonded to the first substrate layer, the channel layer including a microchannel placing the inlet port in fluid communication with the outlet port, and a second substrate layer bonded to the channel layer, the second substrate layer having electrodes printed adjacent to a target zone of the microchannel of the channel layer, wherein the electrodes are configured to raise the temperature of the fluid sample within the target zone of the microchannel when a current is applied thereto.

In another embodiment, the test card includes an adhesive layer between the first substrate layer and the channel layer.

In another embodiment, a height of the test card at the target zone is thinner than a height of the test card surrounding the inlet port.

In another embodiment, the test card includes a third substrate layer between the first substrate layer and the channel layer, the third substrate layer providing a top surface of the microchannel and forming at least part of the outlet port.

In another embodiment, the third substrate forms at least a portion of a mixing chamber located below the inlet port and in fluid communication with the microchannel.

In another embodiment, the electrodes are first electrodes, and which includes second electrodes printed adjacent to a fluid detection zone along the microchannel upstream or downstream of the target zone.

In a general embodiment, a test card for analysing a fluid sample includes at least one substrate, an inlet port formed by a first aperture on a top surface of the at least one substrate, an outlet port formed by a second aperture on the top surface of the at least one substrate, a fluid microchannel formed by an aperture through the at least one substrate placing the inlet port in fluid communication the outlet port, and a circuit printed on a bottom surface of the at least one substrate, the circuit including electrodes printed adjacent to a target zone of the microchannel to provide heating to the target zone to cause a reaction within the target zone when a current is applied thereto.

In another embodiment, the fluid microchannel includes a layer of surfactant.

In another embodiment, the test card includes a mixing chamber formed beneath the inlet port at the top surface of the at least one substrate, the mixing chamber having a larger cross-sectional area than the inlet port.

In another embodiment, the mixing chamber is defined in part by a ledge of the inlet port at the top surface of the at least one substrate.

In another embodiment, the electrodes are first electrodes, and the circuit includes second electrodes printed adjacent to the microchannel at a location upstream or downstream of the target zone.

In another embodiment, the circuit includes a layer of conductive ink printed between the bottom surface of the at least one substrate and a layer of dielectric ink.

In a general embodiment, a method of manufacturing a test card for analysing a fluid sample includes cutting a microchannel into a first polymer material to form a channel layer, cutting at least a first aperture and a second aperture into a second polymer material to form a first substrate layer, bonding the first substrate layer to a first side of the channel layer and a second substrate later to a second side of the channel layer to form a single bonded layer with the microchannel passing therethrough and placing the first aperture and the second aperture in fluid communication with each other, forming a third substrate layer to be thicker than the first substrate layer and the second substrate layer, printing a conductive ink onto a first side of the bonded layer, and adhering the third substrate layer to a second side of the bonded layer opposite the first side.

In another embodiment, the method includes diffusion bonding the first substrate layer to the first side of the channel layer and the second substrate layer to the second side of the channel layer.

In another embodiment, the method includes filling the microchannel with a surfactant solution.

In another embodiment, the method includes filling the microchannel with a surfactant solution including water and then allowing the water to evaporate to leave behind a layer of surfactant molecules on a surface of the microchannel.

In another embodiment, the method includes cutting a third aperture and a fourth aperture into the third substrate layer, and aligning the third aperture with the first aperture and the fourth aperture with the second aperture when adhering the third substrate layer to the bonded layer.

In another embodiment, the method includes cutting the third aperture to have two different cross-sectional areas, a first cross sectional area forming an inlet port on one side of the third substrate layer, and a second cross-sectional area forming at least part of a mixing chamber on an opposite side of the third substrate layer.

In another embodiment, the method includes cutting an analysis port aperture into the third substrate layer, and aligning the analysis port aperture with a target zone of the microchannel when adhering the third substrate layer to the bonded layer.

In another embodiment, the method includes printing a layer of dielectric ink over the conductive ink on the one side of the bonded layer.

BRIEF DESCRIPTION OF THE DRAWINGS

Embodiments of the present disclosure will now be explained in further detail by way of example only with reference to the accompanying figures, in which.

DETAILED DESCRIPTION

Before describing in detail the illustrative system and method of the present disclosure, it should be understood and appreciated herein that the present disclosure relates to a test card for use with a rapid, high sensitivity and high specificity, low complexity diagnostic system using nucleic acid amplification and capable of operating in low resource settings with minimal user training. The system is configured, for example, to cause and analyze a polymerase chain reaction (PCR) within the test card, particularly in the early stages of infection, using a low-cost microfluidic platform employing PCR with a modified DNA polymerase. In an embodiment, the test card is configured to receive about 10 µL of whole blood, the equivalent to a drop of blood obtained from a finger stick. In another embodiment, the fluid sample can be serum, urine, saliva, tears and/or the like.

Figure 1:
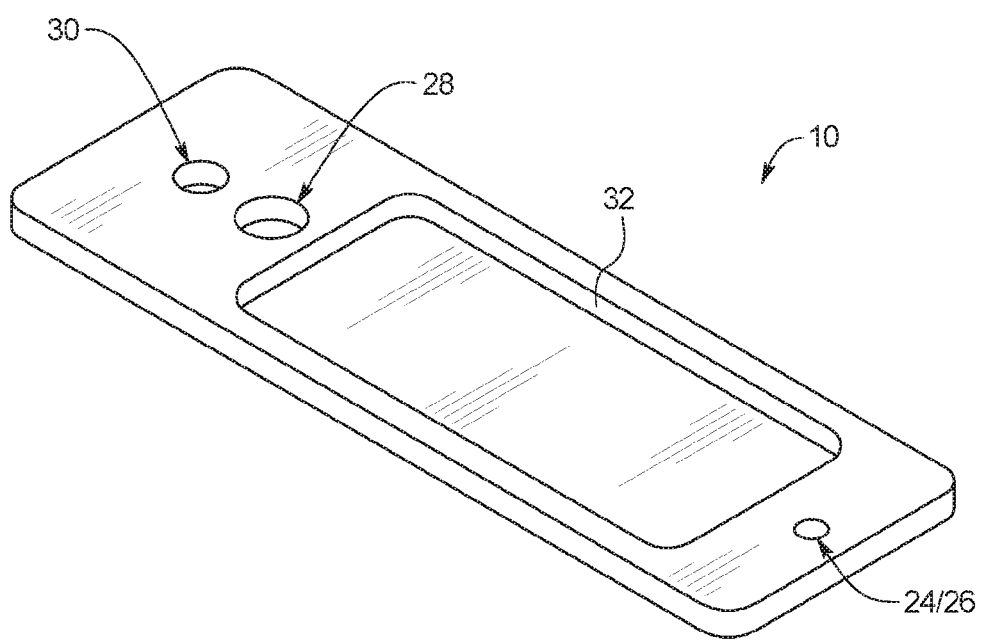
FIG. 1 is a top perspective view of an example embodiment of a test card according to the present disclosure.
Figure 13:
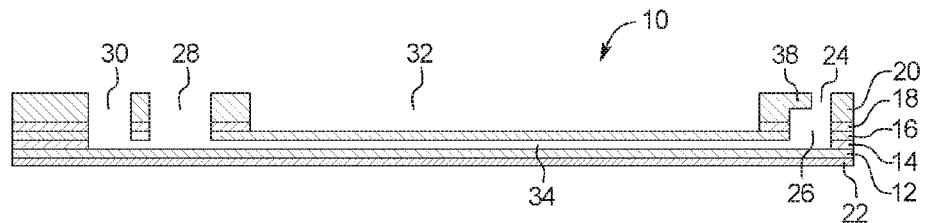
FIG. 13 is a cross-sectional view of the test card of FIG. 1.

FIG. 1 illustrates an example embodiment of a test card 10 according to the present disclosure. As illustrated, test card 10 includes an inlet port 24/mixing chamber 26, a capture port 28, an outlet port 30, and a fluid microchannel 34 (FIG. 13). In use, and as described in more detail below, a fluid sample can be placed into inlet port 24, mixed with one or more reagent in mixing chamber 26, and then pulled though fluid microchannel 34, so that the fluid sample can be analyzed through an analysis port 32 while residing within fluid microchannel 34.

Figure 2:
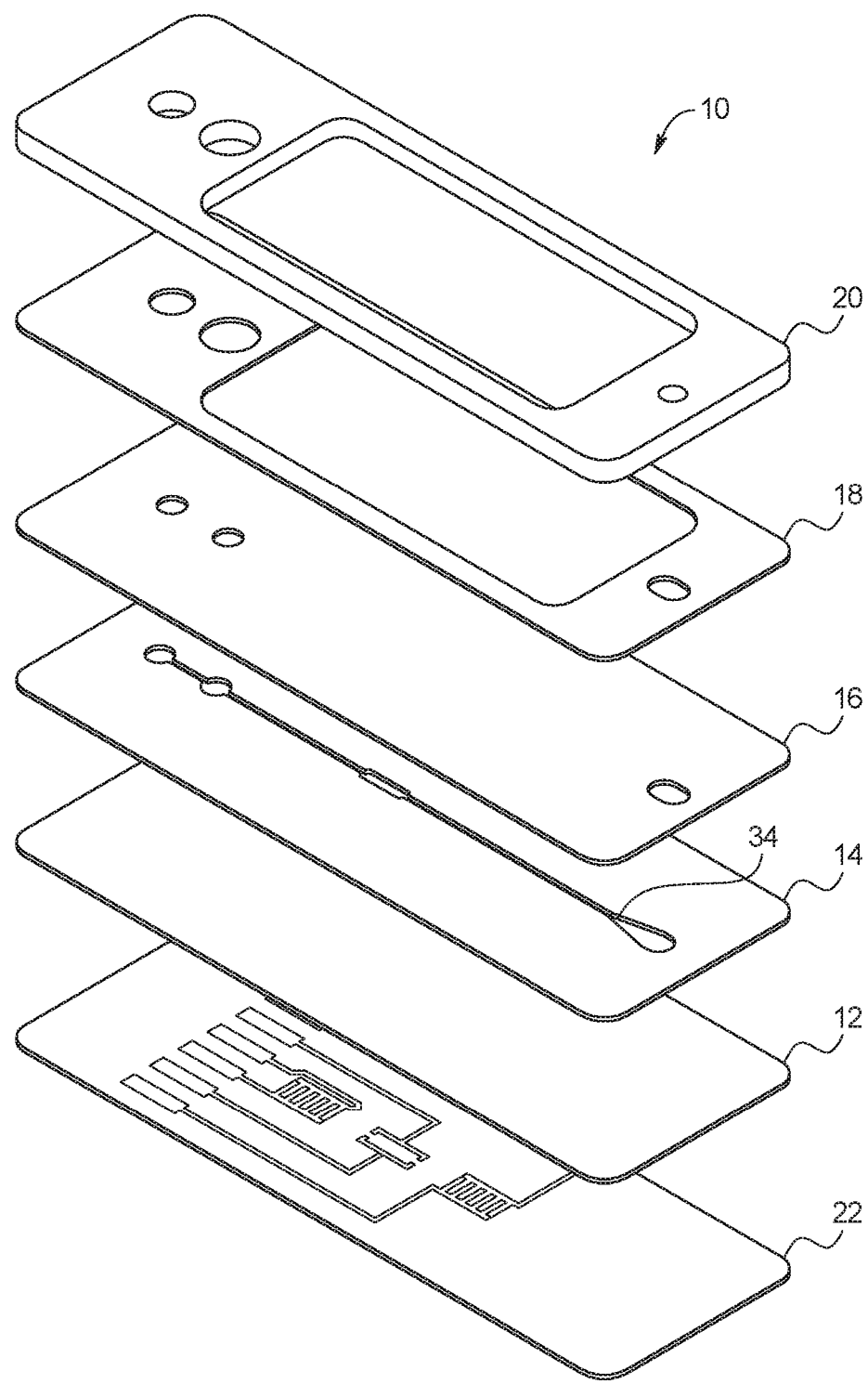
FIG. 2 is an exploded view of the test card of FIG. 1.

FIG. 2 illustrates several layers of substrate material that are combined to form test card 10. As illustrated, test card 10 may include one or more of a bottom substrate layer 12, a channel layer 14, a middle substrate layer 16, an adhesive layer 18, a top substrate layer 20, and a printed circuit layer 22. As explained in more detail below, bottom substrate layer 12, channel layer 14, middle substrate layer 16, adhesive layer 18, and top substrate layer 20 can be optically transparent layers that are bonded together to form inlet port 24/mixing chamber 26, capture port 28, outlet port 30, and fluid microchannel 34, while printed substrate layer 22 can include an ink printed on a bottom surface of bottom substrate layer 12.

Figure 3A:
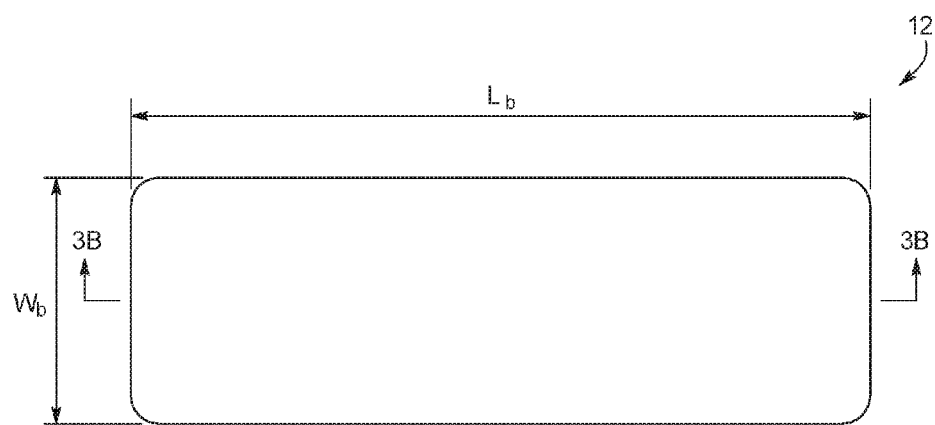
FIG. 3A is a top view of the bottom substrate layer of the test card of FIG. 1.
Figure 3B:
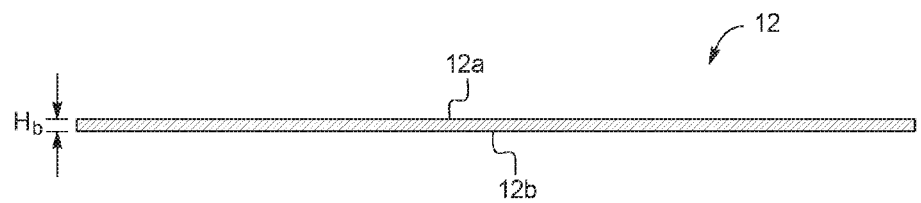
FIG. 3B is a cross-sectional view of the bottom substrate layer of the test card of FIG. 1.

FIGS. 3A and 3B illustrate a top view and a side cross-sectional view, respectively, of bottom substrate layer 12. As illustrated, bottom substrate layer 12 includes a top surface 12a and a bottom surface 12b. As explained in more detail below, test card 10 is formed by bonding top surface 12a to channel layer 14, and by printing printed substrate layer 22 on bottom surface 12b. In an embodiment, bottom substrate layer 12 is cut from a transparent polymer material, for example, a polycarbonate material or another transparent material such as a cyclic olefin copolymer. The material should be resistant to the chemical species that will be placed within test card 10, and should be able to withstand the temperatures reached during a reaction. For example, the material should be able to withstand up to 100+ degrees centigrade without deterioration of the material's mechanical properties. With PCR reactions, the material also must not bind with the DNA or enzymes used. In the illustrated embodiment, bottom substrate layer 12 has a length ($L_b$) of about 3.35 in (8.5 cm), a width ($W_b$) of about 1.10 in (2.8 cm), and a height ($H_b$) of less than 0.01 inch (0.025 cm). Those of ordinary skill in the art will recognize other dimensions that can be used for bottom substrate layer 12.

Figure 4A:
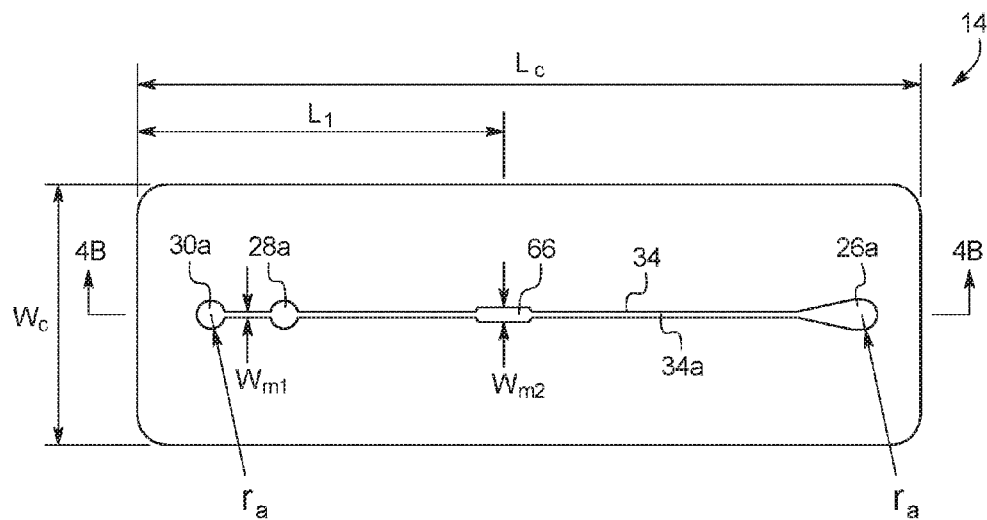
FIG. 4A is a top view of the channel layer of the test card of FIG. 1.
Figure 4B:
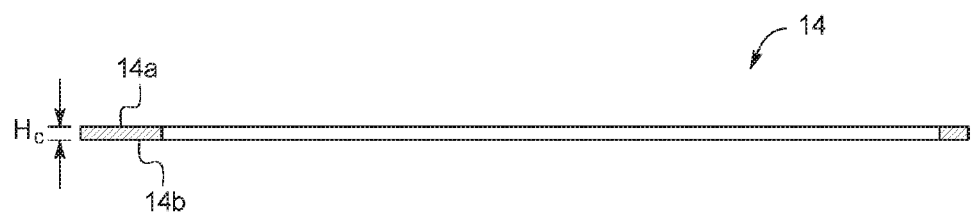
FIG. 4B is a cross-sectional view of the channel layer of the test card of FIG. 1.

FIGS. 4A and 4B illustrate a top view and a side cross-sectional view, respectively, of channel layer 14. As illustrated, channel layer 14 includes a top surface 14a and a bottom surface 14b. As explained in more detail below, test card 10 is formed by bonding top surface 14a to middle substrate layer 16, and by bonding bottom surface 14b to top surface 12a of bottom substrate layer 12. In an embodiment, channel layer 14 is cut from a transparent polymer material, for example, a polycarbonate material or another transparent material such as a cyclic olefin copolymer. The material should be resistant to the chemical species that will be placed within test card 10, and should be able to withstand the temperatures reached during a reaction. For example, the material should be able to withstand up to 100+ degrees centigrade without deterioration of the material's mechanical properties. With PCR reactions, the material also must not bind with the DNA or enzymes used. In the illustrated embodiment, channel layer 14 has a length ($L_c$) of about 3.35 in (8.5 cm), a width ($W_c$) of about 1.10 in (2.8 cm), and a height ($H_c$) of less than 0.01 inch (0.025 cm). Those of ordinary skill in the art will recognize other dimensions that can be used for channel layer 14.

As illustrated, channel layer 14 includes several apertures. Aperture 26a forms a portion of mixing chamber 26, aperture 28a forms a portion of capture port 28, aperture 30a forms a portion of outlet port 30, and aperture 34a forms fluid microchannel 34 when channel layer 14 is bonded to bottom substrate layer 12 and middle substrate layer 16. In the illustrated embodiment, apertures 26a, 28a and 30a have a radius ($r_a$) of about 0.06 in (0.15 cm), microchannel 34 has a width ($w_{m1}$) of about 0.03 in (0.076 cm), and microchannel 34 increases to a width ($w_{m2}$) of about 0.06 in (0.15 cm) at target zone 66. In an embodiment, the length ($L_1$) between the center of target zone 66 and the edge of test card 10 is about 1.65 in (4.2 cm). Those of ordinary skill in the art will recognize other dimensions that can be used for channel layer 14.

Figure 5A:
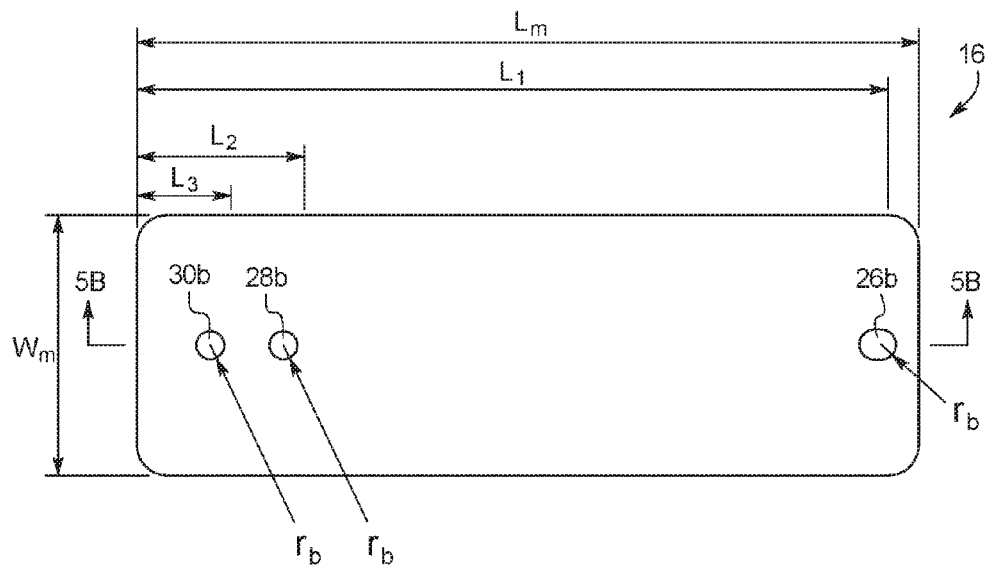
FIG. 5A is a top view of the middle substrate layer of the test card of FIG. 1.
Figure 5B:
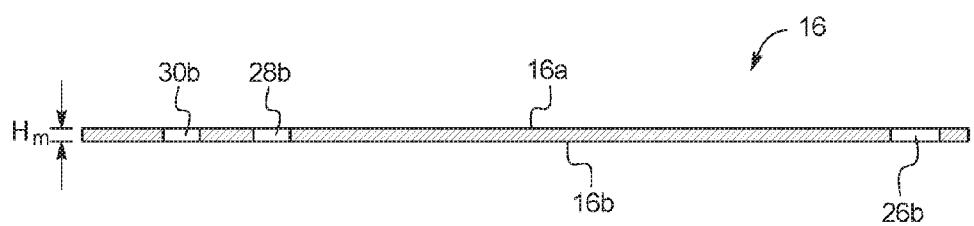
FIG. 5B is a cross-sectional view of the middle substrate layer of the test card of FIG. 1.

FIGS. 5A and 5B illustrate a top view and a side cross-sectional view, respectively, of middle substrate layer 16. As illustrated, middle substrate layer 16 includes a top surface 16a and a bottom surface 16b. As explained in more detail below, test card 10 is formed by bonding top surface 16a to adhesive layer 18 or top substrate layer 20, and by bonding bottom surface 16b to top surface 14a of channel layer 14. In an embodiment, middle substrate layer 16 is cut from a transparent polymer material, for example, a polycarbonate material or another transparent material such as a cyclic olefin copolymer. The material should be resistant to the chemical species that will be placed within test card 10, and should be able to withstand the temperatures reached during a reaction. For example, the material should be able to withstand up to 100+ degrees centigrade without deterioration of the material's mechanical properties. With PCR reactions, the material also must not bind with the DNA or enzymes used. In the illustrated embodiment, channel layer 14 has a length ($L_m$) of about 3.35 in (8.5 cm), a width ($W_m$) of about 1.10 in (2.8 cm), and a height ($H_m$) of less than 0.01 inch (0.025 cm). Those of ordinary skill in the art will recognize other dimensions that can be used for middle substrate layer 16.

As illustrated, middle substrate layer 16 includes several apertures. Aperture 26b forms a portion of mixing chamber 26, aperture 28b forms a portion of capture port 28, aperture 30b forms a portion of outlet port 30. In the illustrated embodiment, apertures 26b, 28b and 30b have a radius ($r_b$) of about 0.06 in (0.15 cm) the length ($L_1$) between aperture 26b and the edge of test card 10 is about 3.18 in (8.1 cm), the length ($L_2$) between aperture 28 band the edge of test card 10 is about 0.71 in (1.8 cm), and the length ($L_3$) between aperture 30b and the edge of test card 10 is about 0.39 in (0.99 cm). Those of ordinary skill in the art will recognize other dimensions that can be used for middle substrate layer 16.

Figure 6A:
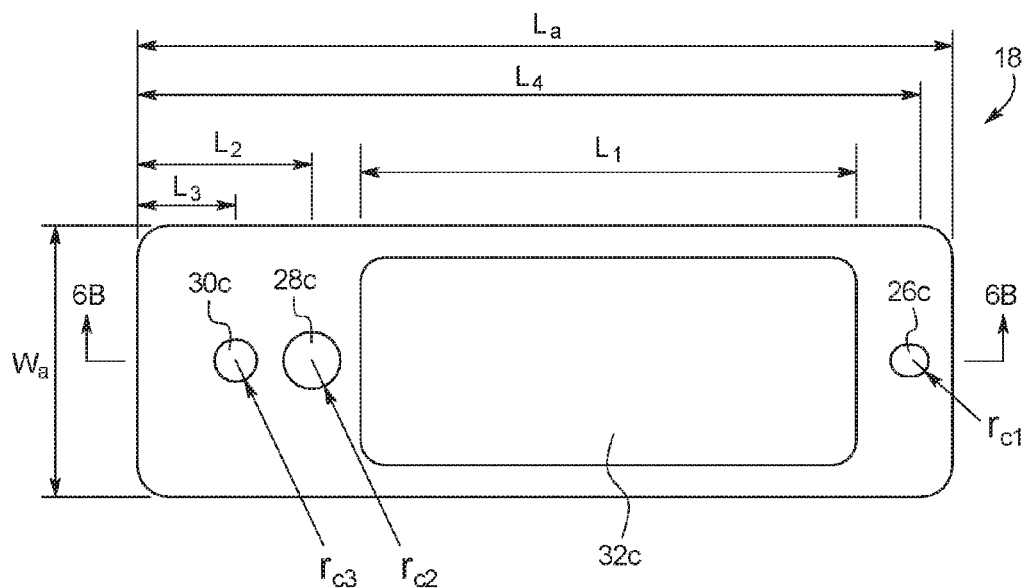
FIG. 6A is a top view of the adhesive layer of the test card of FIG. 1.
Figure 6B:
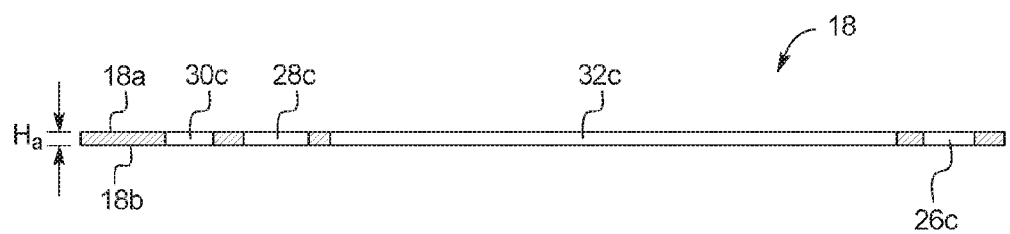
FIG. 6B is a cross-sectional view of the adhesive layer of the test card of FIG. 1.

FIGS. 6A and 6B illustrate a top view and a side cross-sectional view, respectively, of adhesive layer 18. As illustrated, adhesive layer 18 includes a top surface 18a and a bottom surface 18b. As explained in more detail below, test card 10 is formed by bonding top surface 18a to top substrate layer 20, and by bonding bottom surface 18b to top surface 16a of middle substrate layer 16. In an embodiment, adhesive layer 18 is cut from a transparent polymer material, for example, an acrylic based adhesive or another adhesive such as thermal or UV cured epoxies. In the illustrated embodiment, channel layer 14 has a length ($L_a$) of about 3.35 in (8.5 cm), a width ($W_a$) of about 1.10 in (2.8 cm), and a height ($H_a$) of less than 0.01 inch (0.025 cm). Those of ordinary skill in the art will recognize other dimensions that can be used for adhesive layer 18.

As illustrated, adhesive layer 18 includes several apertures. Aperture 26c forms a portion of mixing chamber 26, aperture 28c forms a portion of capture port 28, aperture 30c forms a portion of outlet port 30, and aperture 32c forms a portion of analysis port 32. In the illustrated embodiment, aperture 26c has a radius ($r_{c1}$) of about 0.06 in (0.15 cm), aperture 28c has a radius ($r_{c2}$) of about 0.12 in (0.30 cm), aperture 30c has a radius ($r_{c3}$) of about 0.09 in (0.23 cm), the length ($L_1$) of aperture 32c is about 2.04 in (5.2 cm), the length ($L_2$) between aperture 28c and the edge of test card 10 is about 0.71 in (1.8 cm), the length ($L_3$) between aperture 30c and the edge of test card 10 is about 0.39 in (0.99 cm), and the length ($L_4$) between aperture 26c and the edge of test card 10 is about 3.18 in (8.1 cm). Those of ordinary skill in the art will recognize other dimensions that can be used for adhesive layer 18.

The purpose of adhesive layer 18 is to bond middle substrate layer 16 to top substrate layer 20. In an alternative embodiment, as will be understood from the description below, test card 10 can be formed without adhesive layer 18, by bonding the top surface 16a of middle substrate layer 16 directly to the bottom surface 20b of top substrate layer 20.

Figure 7A:
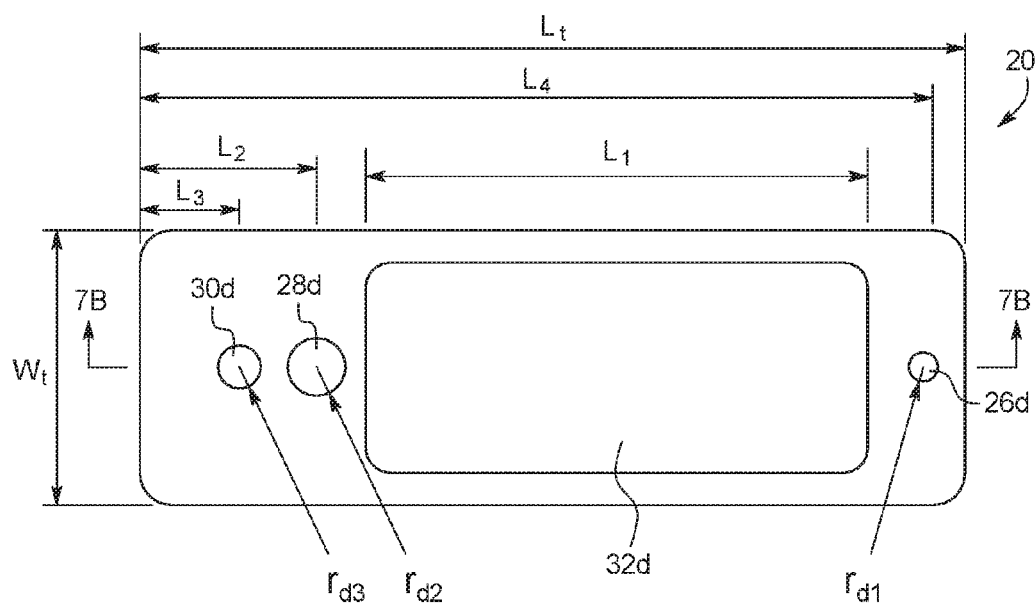
FIG. 7A is a top view of the top substrate layer of the test card of FIG. 1.
Figure 7B:
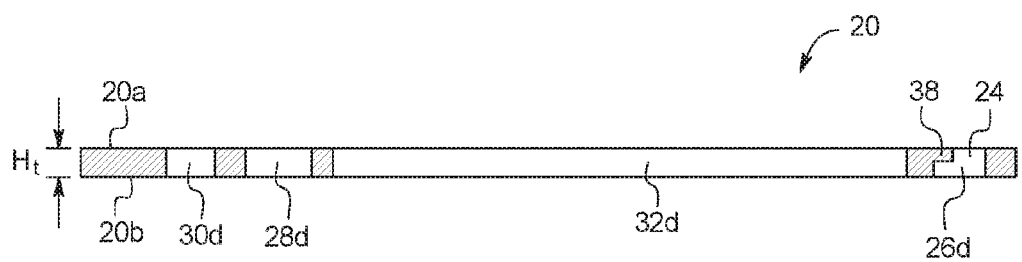
FIG. 7B is a cross-sectional view of the top substrate layer of the test card of FIG. 1.

FIGS. 7A and 7B illustrate a top view and a side cross-sectional view, respectively, of top substrate layer 20. As illustrated, top substrate layer 20 includes a top surface 20a and a bottom surface 20b. As explained in more detail below, test card 10 is formed by bonding bottom surface 20b to top surface 16a of middle substrate layer 16 or to top surface 18a of adhesive layer 18. In an embodiment, top substrate layer 20 is cut from a polymer material, for example, polycarbonate, cyclic olefin copolymer, polyethylene, etc. In an embodiment, top substrate layer 20 is transparent, but top substrate layer 20 does not necessarily have to be transparent because analysis port 32 allows a PCR reaction to be viewed within microchannel 34 even if top substrate layer 20 is not transparent. In the illustrated embodiment, top substrate layer 20 has a length ($L_t$) of about 3.35 in (8.5 cm), a width ($W_t$) of about 1.10 in (2.8 cm), and a height ($H_t$) of about 0.09 in (0.23 cm). Those of ordinary skill in the art will recognize other dimensions that can be used for top substrate layer 20.

As illustrated, top substrate layer 20 includes several apertures. Aperture 26d forms inlet port 24 and a portion of mixing chamber 26, aperture 28d forms a portion of capture port 28, aperture 30d forms a portion of outlet port 30, and aperture 32d forms a portion of analysis port 32. In the illustrated embodiment, aperture 26d has a radius ($r_{d1}$) of about 0.06 in (0.15 cm), aperture 28d has a radius ($r_{d2}$) of about 0.12 in (0.3 cm), aperture 30d has a radius ($r_{d3}$) of about 0.09 in (0.23 cm), the length ($L_1$) of aperture 32d is about 2.04 in (5.2 cm), the length ($L_2$) between aperture 28d and the edge of test card 10 is about 0.71 in (1.8 cm), the length ($L_3$) between aperture 30d and the edge of test card 10 is about 0.39 in (0.99 cm), and the length ($L_4$) between aperture 26d and the edge of test card 10 is about 3.18 in (8.1 cm). Those of ordinary skill in the art will recognize other dimensions that can be used for top substrate layer 20.

As illustrated in FIG. 7B, aperture 26d is formed of two different lengths, creating a ledge 38 at top surface 20a. The top of aperture 26d with the smaller surface area from a top or bottom view at top surface 20a forms inlet port 24, and the bottom of aperture 26d, below ledge 38 with the larger surface area from a top or bottom view, forms a portion of mixing chamber 26. It has been determined that this configuration is advantageous for several reasons. For example, the larger top surface area of mixing chamber 26 improves the ability of a fluid sample inserted into inlet port 24 to be mixed with a reagent. The larger top surface area improves sample mixing by increasing the total volume and length scale of the fluid, allowing the fluid to mix via inertial mixing rather than purely diffusive mixing. In an embodiment, when the loading port in preloaded with one or more reagent and a patient sample is added on top of the preloaded reagent, the size of the loading port determines the size of the mixing interface between the two fluids. This size allows for the determination of the exact mixing ratio of the two fluids thus ensuring a proper reaction can occur. When the one or more reagent is PCR master mix, by controlling the loading port size, the ratio of raw sample to PCR master mix can be controlled precisely at the fluid interface allowing for a correct PCR reaction. Additionally, ledge 38 reduces the formation of bubbles entering microchannel 34 by increasing the needed energy to move the bubble from the inlet port into the microfluidic channel. This occurs because of the increase in internal pressure required to decrease a bubbles' size to clear the ledge.

Figure 8A:
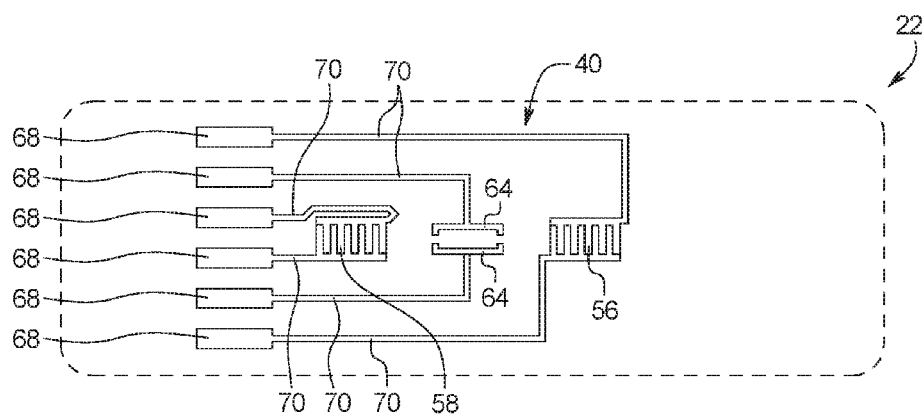
FIG. 8A is a top view of the printed circuit layer of the test card of FIG. 1 with dielectric ink omitted for clarity.
Figure 8B:
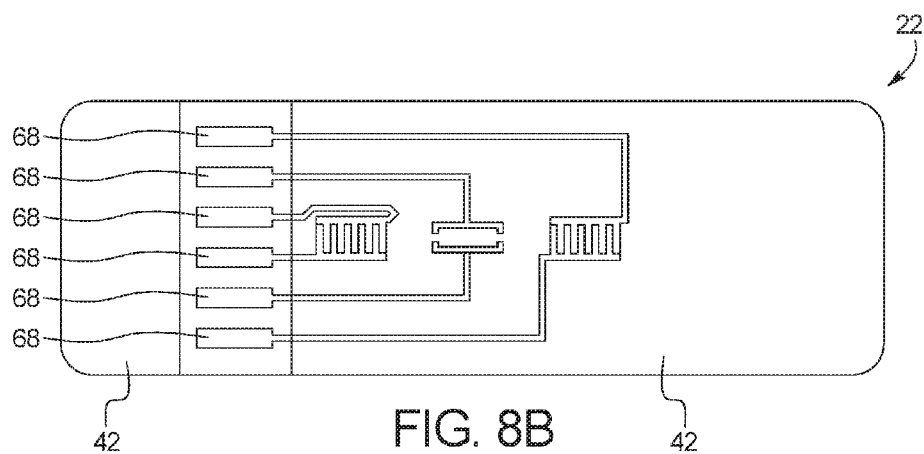
FIG. 8B is a top view of the printed circuit layer of the test card of FIG. 1 with dielectric ink shown.
Figure 8C:
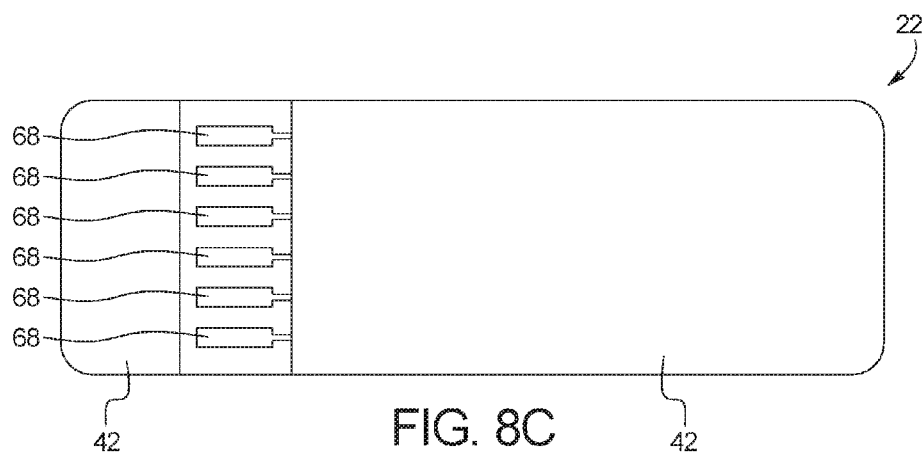
FIG. 8C is a bottom view of the printed circuit layer of the test card of FIG. 1 with dielectric ink shown.

FIG. 8A illustrates a top view of a printing arrangement of printed substrate layer 22. In FIG. 8, only conductive ink 40 is shown, and dielectric ink 42 has been omitted for simplicity. FIG. 8B shows the top view of FIG. 8A with dielectric ink 42. FIG. 8C illustrates a bottom view of a printing arrangement of printed substrate layer 22, with dielectric ink 42 printed over conductive ink 40.

In the illustrated embodiment, printed substrate layer 22 is printed on bottom surface 12b of bottom substrate layer 12. As illustrated, printed substrate layer 22 is printed with a conductive ink 40 and a dielectric ink 42. The conductive ink 40 forms the electrical components of test card 10, whereas the dielectric ink 42 serve as protective, non-conductive coating to encapsulate the electrical components. The conductive ink 40 becomes the electrical components once it is cured, for example, by heat or ultraviolet light. The specific components of printed substrate layer 22 are discussed in more detail below.

The manufacture of test card 10 will now be described with reference to the elements shown in FIGS. 1 to 8. Though the manufacturing steps below are described in a particular order, those of ordinary skill in the art will recognize that the order of several of the steps can be changed to accomplish the same result. It should also be understood that although manufacture of test card 10 is described below in relation to a batch process that bonds multiple bottom substrate layers 12, channel layers 14, middle substrate layers 16, adhesive layers 18, top substrate layers 20, and/or printed circuit layers 22 at the same time to create a plurality of test cards 10, the same process can be employed to bond a single bottom substrate layer 12, a single channel layer 14, a single middle substrate layer 16, a single adhesive layer 18, a single top substrate layer 20, and/or a single printed circuit layer 22 to create a single test card.

Manufacture of test card 10 begins by cutting the apertures of each of channel layer 14 and middle substrate layer 16 into separate sheets of polymer material. Apertures 26a, 28a, 30a and 34a are cut into a layer of polymer material 46 for channel layer 14. Apertures 26b, 28b and 30b are cut into a layer of polymer material 48 for middle substrate layer 16.

Various methods can be used to cut the apertures into the layers of polymer material. For example, the apertures may be cut by laser ablation, knife cutting with plotting machines, or die cutting. Table 1 below illustrates the advantages and disadvantages of various cutting methods.

TABLE 1

| Method | Line Width | Design Flexibility | Speed | Investment | Process Complexity |
|---|---|---|---|---|---|
| Laser Ablation | >30 μm | High | Fast | High | High |
| Knife Cutting | >600 μm | High | Moderate | Moderate | Low |
| Die Cutting | >600 μm | Low | Fast | Moderate | Moderate |

As illustrated above, laser ablation is the only method that provides a resolution lower than 600 μm. Knife cutting and die cutting are less complex and lower in initial cost, but do not provide the same design flexibility at smaller line widths. Laser ablation also provides the ability to cut three-dimensional apertures by only cutting part of the depth of a polymer sheet, which allows the length and/or width of the apertures to be varied through a single polymer sheet.

Figure 9:
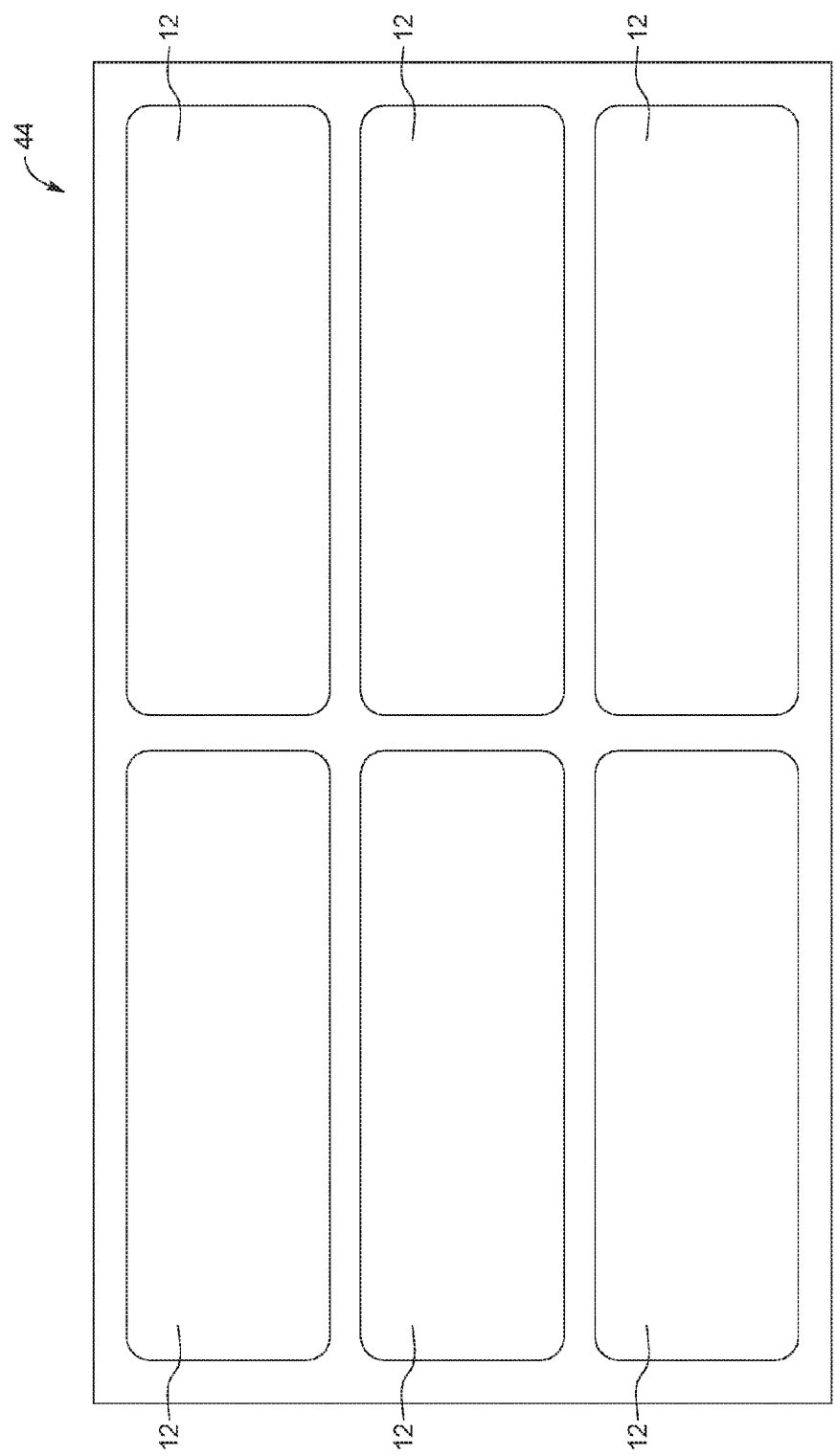
FIG. 9 is a top view of an example embodiment of a first polymer sheet including a plurality of bottom substrate layers.
Figure 10:
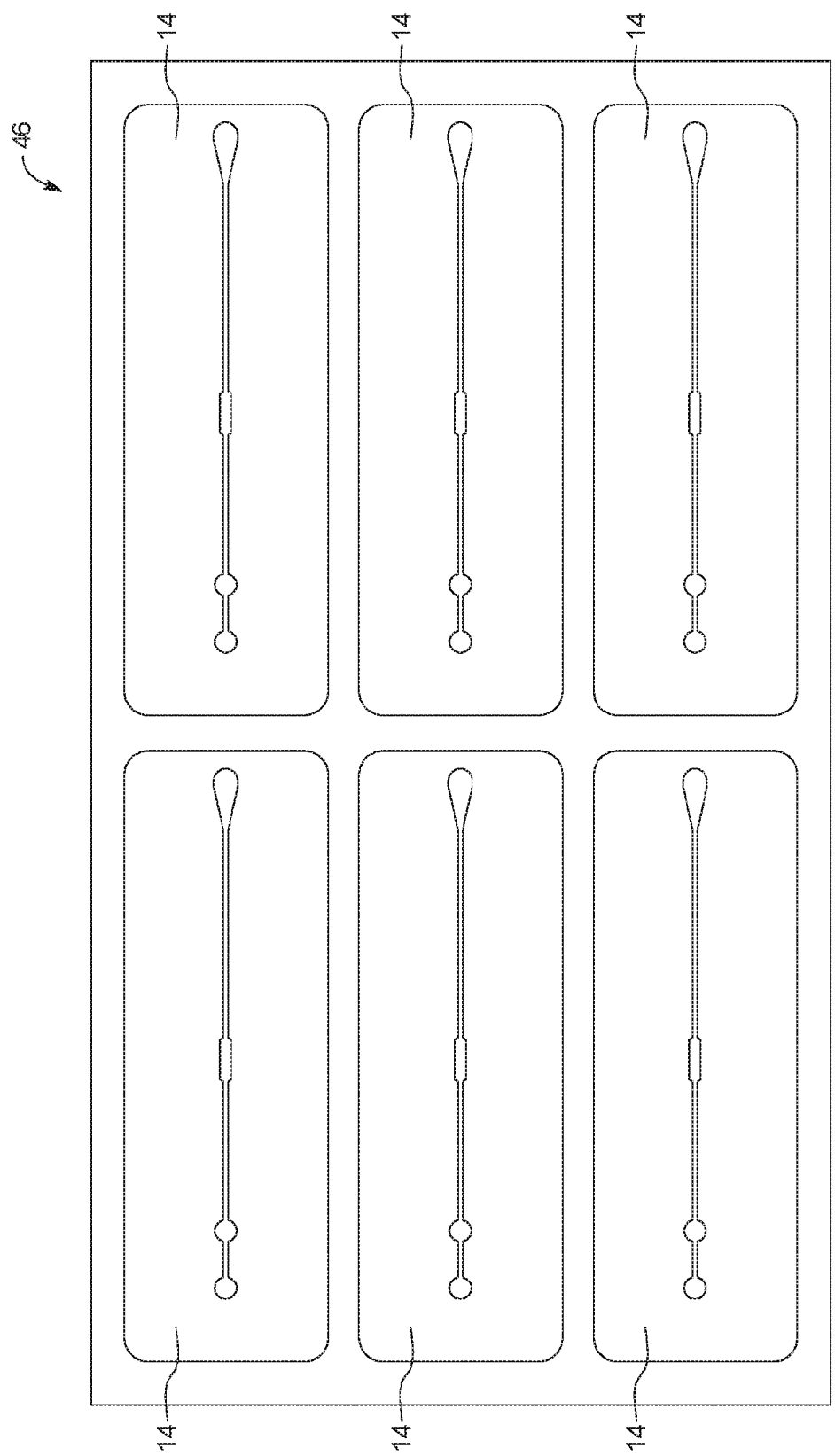
FIG. 10 is a top view of an example embodiment of a second polymer sheet including a plurality of channel layers.
Figure 11:
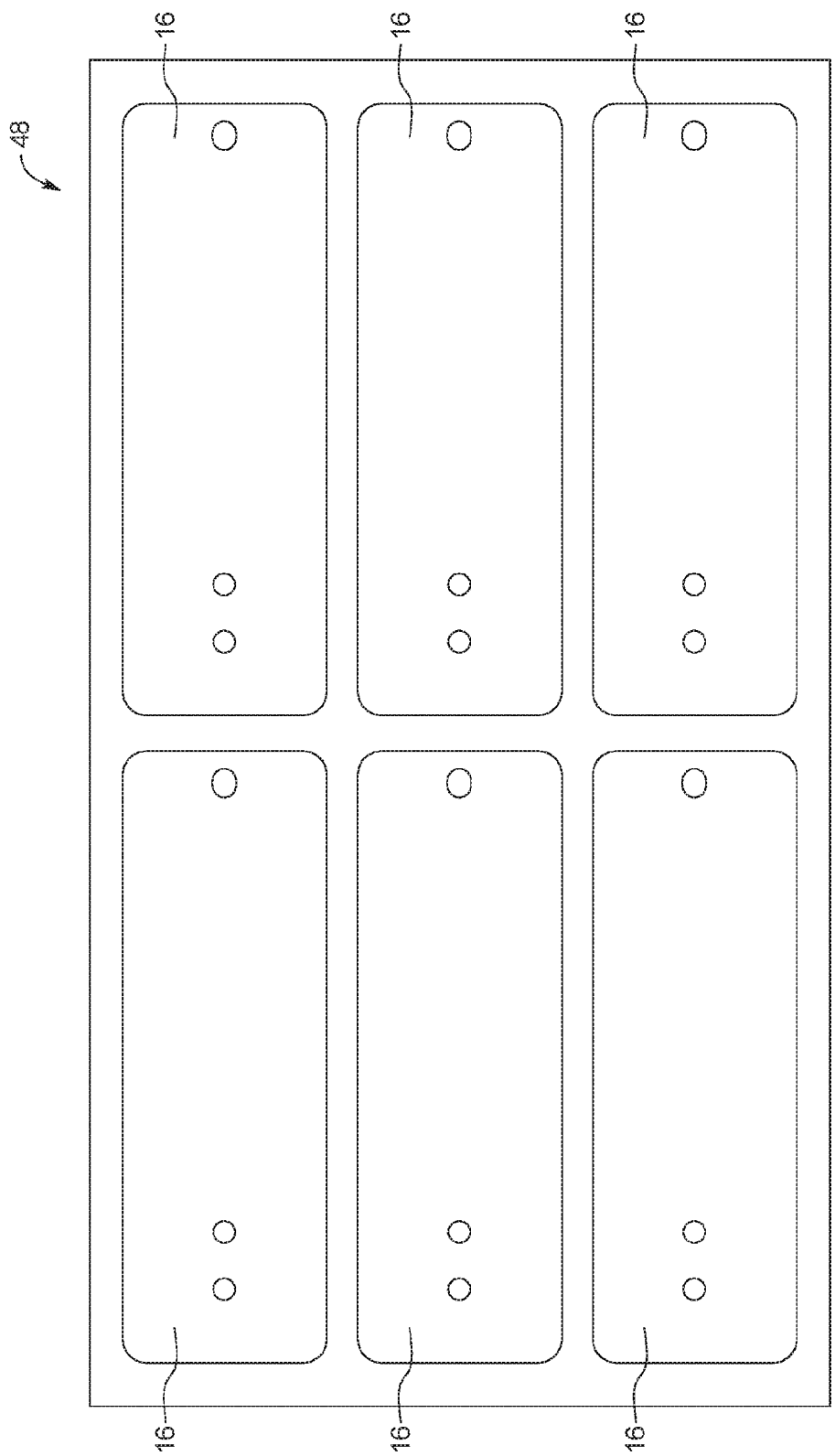
FIG. 11 is a top view of an example embodiment of a third polymer sheet including a plurality of middle substrate layers.

FIG. 9 shows an example embodiment of a first polymer sheet 44 for a plurality of bottom substrate layers 12. FIG. 10 shows an example embodiment of a second polymer sheet 46 for a plurality of channel layers 14 after cutting apertures 26a, 28a, 30a and 34a. FIG. 11 shows an example embodiment of a third polymer sheet 48 for a plurality of middle substrate layers 16 after cutting apertures 26b, 28b and 30b. In the illustrated embodiment, polymer sheets 44, 46, 48 are about ten inches long and about six inches wide and are designed to manufacture six test cards 10. Those of ordinary skill in the art will recognize that any number of test cards can be manufactured using polymer sheets 44, 46, 48.

After first polymer sheet 44, second polymer sheet 46 and third polymer sheet 48 are formed, first polymer sheet 44, second polymer sheet 46 and third polymer sheet 48 are bonded into a single layer to form fluid microchannel 34. The bonding can be, for example, diffusion bonding or adhesive bonding. Those of ordinary skill in the art will recognize other methods for bonding together first polymer sheet 44, second polymer sheet 46 and third polymer sheet 48. Further, as explained above, a single bottom substrate layer 12, a single channel layer 14 and a single middle substrate layer 16 can be bonded in the same manner. It should further be understood that bonding two separate layers of material as described herein can include directly bonding one layer to another layer by pressing a surface of the one layer against a surface of the other layer, or indirectly bonding one layer to another layer by inserting an intermediate layer between the one layer and the other layer.

In an embodiment, first polymer sheet 44, second polymer sheet 46 and third polymer sheet 48 can be diffusion bonded by placing first polymer sheet 44, second polymer sheet 46 and third polymer sheet 48 together under elevated pressure and temperature conditions, so that molecules from first polymer sheet 44, second polymer sheet 46 and third polymer sheet 48 diffuse across the interfaces between layers. The molecular-level bonds bond the layers together as one material. In an embodiment, first polymer sheet 44, second polymer sheet 46 and third polymer sheet 48 can be placed together under an elevated pressure of, for example, 100 PSI in the case of polycarbonate. For other materials, it is important that the pressure be maintained such that there is minimal material deflection for the given temperature. Ideally the pressure should be below the materials given load of the heat deflection temperature and below the polymer's glass transition temperature. In the case of polycarbonate, the temperature should be below about 145 degrees centigrade. The time is determined by the material, such that the molecules between the layers have had sufficient time to diffuse between each other. In the case of polycarbonate, the bonding time is approximately 25 minutes. During the entire bonding process, including cooling of the bonded polymer layers, the layers should remain under isobaric conditions. Those of ordinary skill in the art will recognize other rates, times, temperatures and pressures that can be used for diffusion bonding. Those of ordinary skill in the art will further recognize that the rates, times, temperatures and pressures will vary depending upon the material chosen for first polymer sheet 44, second polymer sheet 46 and third polymer sheet 48.

In an alternative embodiment, first polymer sheet 44, second polymer sheet 46 and third polymer sheet 48 can be adhesively bonded together using an adhesive, for example, an acrylic adhesive such as 3M 200MP or similar. In addition, thermal and UV cure epoxies can be used. Adhesive bonding can be accomplished by placing an adhesive on the top and/or bottom surfaces of first polymer sheet 44, second polymer sheet 46 and third polymer sheet 48, or can be accomplished by placing separate adhesive layers between first polymer sheet 44, second polymer sheet 46 and third polymer sheet 48. If adhesive layers are placed between first polymer sheet 44, second polymer sheet 46 and third polymer sheet 48, the adhesive layers may need apertures corresponding to the apertures cut into the sheets.

After the bonding process is complete, a single sheet of material 50 is formed from the first polymer sheet 44, second polymer sheet 46 and third polymer sheet 48. The single sheet of material 50 is processed to remove trapped air pockets using a degassing procedure, in which the single sheet of material 50 formed from first polymer sheet 44, second polymer sheet 46 and third polymer sheet 48 is placed in a vacuum chamber at an elevated temperature. In an embodiment, the single sheet of material 50 is placed in a vacuum chamber at a temperature of 130 degrees centigrade for polycarbonate. For other polymers the temperature should remain below the maximum rated working temperature of the material.

Figure 12:
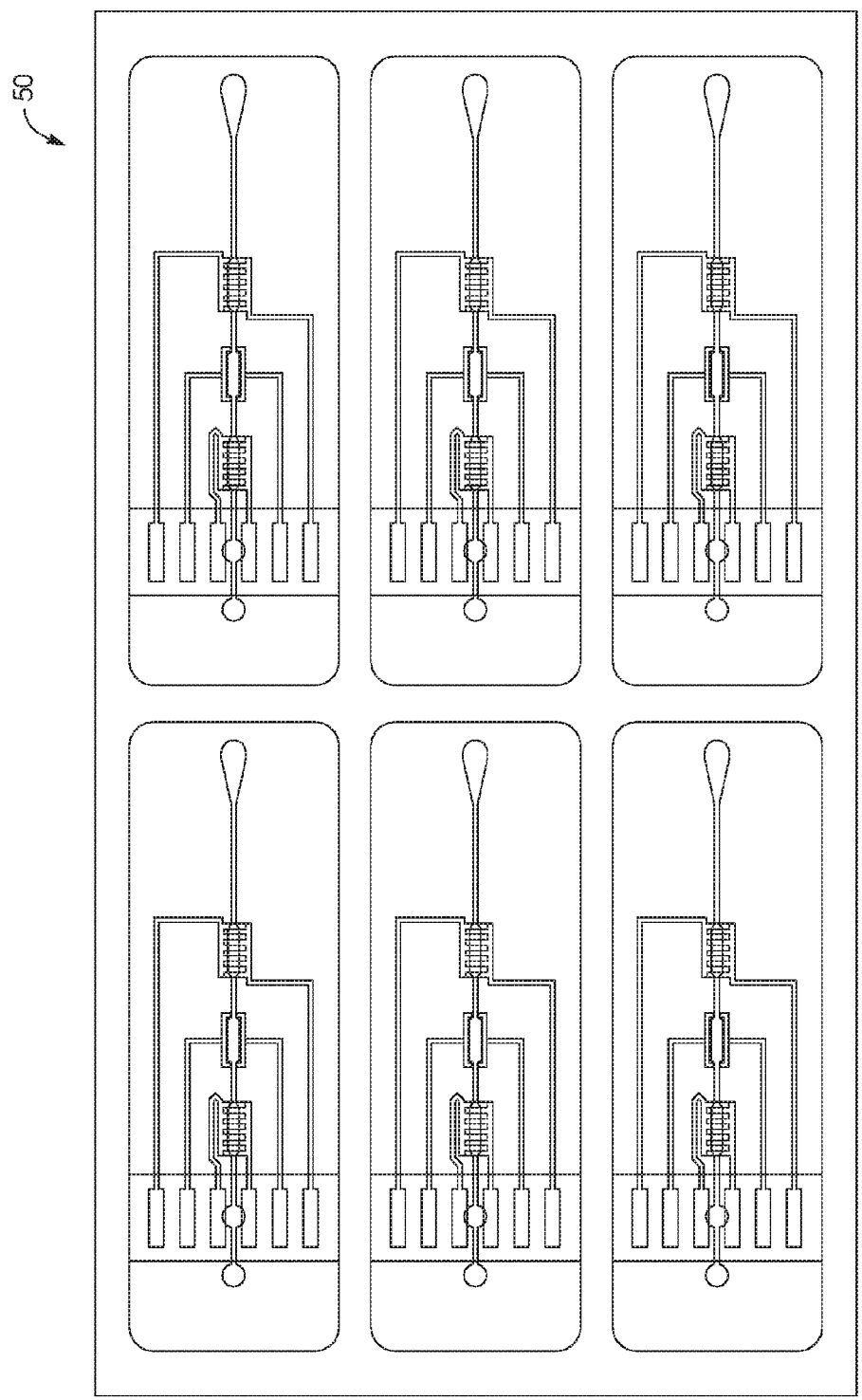
FIG. 12 is a top view of the single sheet of material with a plurality of printed circuit layers printed on a bottom surface thereof.

Once the single sheet of material 50 is formed, one or more printed circuit layer 22 is screen printed on a bottom surface of the single sheet of material 50. FIG. 12 shows a top view of the single sheet of material 50 with a plurality of printed circuit layers 22 printed on the bottom surface thereof. Because the first polymer sheet 44, second polymer sheet 46 and third polymer sheet 48 are transparent in the illustrated embodiment, the plurality of printed circuit layers 22 are visible from the top view. To print the plurality of printed circuit layers 22 on the single sheet of material 50, the conductive ink 40 forming the electrical components of the test cards 10 is first printed on the bottom surface, and the dielectric ink 42 serving as the protective, non-conductive coating is then printed over the conductive ink 40.

The conductive ink 40 and dielectric ink 42 can be cured, for example, by heat or ultraviolet light, to form the electrical components of test card 10. In an embodiment, one or more layers of conductive ink is printed and then cured, and then one or more layers of dielectric ink 42 is printed and cured. In another embodiment, both the conductive ink 40 and the dielectric ink 42 are printed, and then both the conductive ink 40 and the dielectric ink 42 are cured. In another embodiment, several alternating layers of conductive ink 40 and dielectric ink 42 are printed to create multiple levels of conductive elements.

In an embodiment, printed circuit layer 22 is screen printed on a bottom surface of the single sheet of material 50 through a screen made of a stainless steel or a polymer mesh. A hardened emulsion can be used to block out all areas of the screen except for the desired print pattern for the conductive ink 40 and/or dielectric ink 42, so that the conductive ink 40 and/or dielectric ink 42 is pushed through the screen in the desired print pattern.

Once the single sheet of material 50 has been formed and printed circuit layer 22 is printed on the single sheet 50, the single sheet can be cut into a plurality of individual sheets for individual test cards 10. The individual sheets can then be attached to top substrate layers 20 by adhesive layers 18, or can be bonded directly to top substrate layers 20 without adhesive layers 18.

In an embodiment, top substrate layer 20 is significantly thicker than bottom substrate layer 12, channel layer 14 and middle substrate layer 16, to provide depth and rigidity for test card 10, for example, to provide depth to the mixing chamber 26, capture port 28 and outlet port 30, and to provide depth to test card 10 to allow test card 10 to interface with larger devices, for example, the device disclosed in U.S. application Ser. No. 15/185,640, entitled "Device for Analyzing a Fluid Sample and Use of Test Card with Same", noted above. In an embodiment, top substrate layer 20 and the apertures therein can be formed by injection molding and/or machining various polymer materials such as polycarbonate or a similar material.

After test card 10 is fully assembled, a coating process is applied to the surfaces of fluid microchannel 34. First, fluid microchannel 34 is filled with surfactant solution diluted with water to a desired concentration. The surfactant solution can include, for example, 10% Triton X-100. The desired concentration is relative to a concentration in which surfactant molecules begin to aggregate in solution, called the critical micelle concentration ("CMC").

After fluid microchannel 34 is filled with surfactant solution, the water solvent is allowed to evaporate, leaving behind a layer of surfactant molecules on the surfaces of fluid microchannel 34. The density of the deposited layer of surfactant molecules depends on the concentration of the original solution. In an embodiment, 0.1% Triton X-100 can be used to generate a molecular monolayer of surfactant on the microchannel walls.

The deposited surfactant is advantageous, for example, because it affects the wettability (or surface tension) in relation to the fluid sample that flows through test card 10 during use. That is, the surfactant can be used to modify the wettability (or surface tension) of fluid microchannel 34. The increased wettability (or surface tension) allows for smoother fluid loading and helps prevent bubble formation of the fluid sample when fluid microchannel 34 is exposed to elevated temperatures.

FIG. 13 shows a cross-sectional view of a fully assembled test card 10. In FIG. 13, the heights of bottom substrate layer 12, channel layer 14, middle substrate layer 16, adhesive layer 18 and printed circuit layer 22 relative to top substrate layer 20 have been increased for illustrative purposes. As explained above, top substrate layer 20 is significantly thicker (e.g., greater than 10× thicker) than the rest of the layers to provide depth and rigidity to test card 10.

As illustrated, inlet port 24 and mixing chamber 26 are formed by apertures 26a, 26b, 26c and 26d in channel layer 14, middle substrate layer 16, adhesive layer 18 and top substrate layer 20, respectively. Capture port 28 is formed by apertures 28a, 28b, 28c and 28d in channel layer 14, middle substrate layer 16, adhesive layer 18 and top substrate layer 20, respectively. Outlet port 30 is formed by apertures 30a, 30b, 30c and 30d in channel layer 14, middle substrate layer 16, adhesive layer 18 and top substrate layer 20, respectively. Fluid microchannel 34 is formed by aperture 34a in channel layer 14, top surface 12a of bottom substrate layer 12, and bottom surface 16b of middle substrate layer 16. Analysis port 32 is formed by apertures 32c and 32d in adhesive layer 18 and top substrate layer 20, respectively. As illustrated, in the assembled test card, inlet port 24, capture port 28, outlet port 30 and analysis port 32 are each open at the top surface 20a of test card 10.

In use, a fluid sample can be injected into inlet port 24 at the top surface 20a of top substrate layer 20 for processing through test card 10. The fluid sample then flows through inlet port 24 to mixing chamber 26 located directly below inlet port 24. As explained above, top substrate layer 20 is cut at a first length at top surface 20a and a second, greater length at bottom surface 20b to create a ledge 38 that causes mixing chamber 26 to have more horizontal surface area that inlet port 24, which allows a fluid sample injected into inlet port 24 to be mixed thoroughly and traps bubbles before the bubbles can enter fluid microchannel 34. In an embodiment, mixing chamber 26 is configured to receive about 10 μL of whole blood through inlet port 24, the equivalent to a drop of blood obtained from a finger stick. The low volume of fluid sample equates to a lower quantity of reagents required for the PCR reaction, in turn dramatically reducing the cost of the PCR reagents.

The fluid sample can be mixed with a reagent mix before being pulled through microchannel 34. In an embodiment, the reagent mix can be stored in mixing chamber 26 prior to the introduction of the fluid sample through inlet port 24. In an alternative embodiment, the reagent mix can be injected into mixing chamber 26 through inlet port 24 before or after the fluid sample is injected into inlet port 24.

When the fluid sample is mixed with the reagent mix, it is important to have a correct ratio of fluid sample to final PCR volume, because if the correct ratio is not maintained, the PCR will take too long or fail. In test card 10, the geometry of mixing chamber 26 has been optimized to mix the patient sample with the reagent mix. The size of mixing chamber 26 allows for the determination of the exact mixing ratio of the two fluids thus ensuring a proper reaction can occur. In the case of a PCR master mix, by controlling the loading port size, the ratio of raw sample to PCR master mix can be controlled precisely at the fluid interface allowing for a correct PCR reaction. In an embodiment, the exact ratio desired is between 10-20% of the PCR reaction containing raw sample.

Once the fluid sample is loaded into mixing chamber 26, the fluid sample can be pulled through fluid microchannel 34 by a vacuum pressure applied to outlet port 30. As explained above, fluid microchannel 34 is formed by a lengthwise aperture 34a cut into channel layer 14 and is configured to place inlet port 24 and mixing chamber 26 in fluid communication with capture port 28 and outlet port 30. In use, a vacuum source can be placed against the top surface 20a of top substrate layer 20 at outlet port 30. When a negative pressure is applied to outlet port 30, the vacuum pressure pulls the fluid sample from mixing chamber 28 through fluid microchannel 34 so that the fluid sample can be analyzed through analysis port 32 while residing within target zone 66 of microchannel 34. The analysis of the fluid sample is described in more detail below.

Capture port 28 is configured to capture fluid from the fluid sample before the fluid flows to outlet port 30. In the illustrated embodiment, capture port 28 is sized to allow fluid to build up before it can reach outlet port 30 to prevent the fluid from being sucked out of outlet port 30 by the vacuum pressure applied to outlet port 30. In an embodiment, capture port can include a porous material which can act like a sponge to absorb any excess fluid and prevent fluid from escaping from test card 10 due to mishandling.

Figure 14:
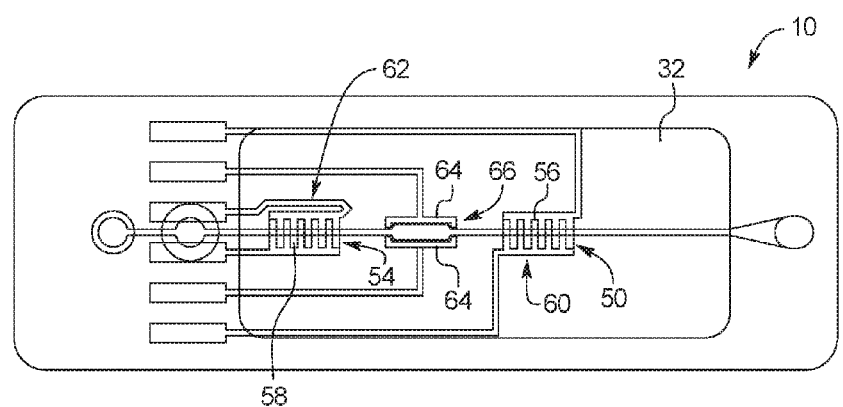
FIG. 14 is a top view of the test card of FIG. 1 with dielectric ink omitted for clarity.

FIG. 14 shows a top view of a fully assembled test card 10. Because the bottom substrate layer 12, channel layer 14, middle substrate layer 16, adhesive layer 18, and top substrate layer 20 are transparent in the illustrated embodiment, printed circuit layer 22 is visible from the top view. In FIG. 14, the dielectric ink 42 on the bottom of test card 10 has been omitted for simplicity FIG. 14 illustrates the alignment of the elements of printed circuit layer 22 with fluid microchannel 34. As illustrated, fluid microchannel 34 includes a first fluid detection zone 50, a target zone 66 and a second fluid detection zone 54. First fluid detection zone 50 is aligned with screen printed electrodes 56 downstream from mixing chamber 26, while second fluid detection zone 54 is aligned with screen printed electrodes 58 downstream from target zone 66. First fluid detection zone 50 and second fluid detection zone 54 are used to determine whether the fluid sample has flowed through fluid microchannel 34 so that the fluid can be analyzed within target zone 66.

By screen printing electrodes 56, 58 below first fluid detection zone 50 and/or second fluid detection zone 54, capacitive sensors 60, 62 are created, where the capacitor dielectric material is composed of the fluid sample contained in fluid microchannel 34 and the material surrounding fluid microchannel 34. The dielectric constant of the capacitive sensors 60, 62 changes as fluid flows through microchannel 34, which allows for measurements to be made at first fluid detection zone 50 and/or second fluid detection zone 54. In an embodiment, capacitive sensor 60, 62 can be used to detect whether or not the fluid sample is present within first fluid detection zone 50 and/or second fluid detection zone 54, as the dielectric constant of capacitive sensors 60, 62 differs considerably when there is liquid in the microchannel at capacitive sensors 60, 62.

In an alternative embodiment, capacitive sensors 60, 62 can be used to detect a chemical species of interest in the fluid sample based on the measured dielectric value. For example, during a PCR reaction there is initially very little DNA present, so there is a specific dielectric value and the capacitive sensors 60, 62 can read a specific value for capacitance. As the PCR reaction progresses, the dielectric value changes as more DNA is produced, in turn changing the capacitance detected by capacitive sensors 60, 62. Based on the change in capacitance, a user can determine the amount of DNA created during the PCR reaction.

Screen printed electrodes 64 are also aligned with target zone 66 of fluid microchannel 34. When a voltage is applied to electrodes 64, the current across electrodes 64 heats the fluid sample within target zone 66 of fluid microchannel 34 to cause a PCR to occur. The PCR can be analyzed by a user or controller to determine, for example, whether the fluid sample tests positive or negative for a particular bacteria or virus.

In the illustrated embodiment, target zone 66 is located within the borders of analysis port 32 when viewed from the top. An advantage of this embodiment is that analysis port 32 thins the height of test card 10 at and around target zone 66, which allows an assay within target zone 66 to be viewed clearly. The thin height at target zone 66 also allows the fluid within target zone 66 to be heated or cooled more quickly than it would in a thicker section without analysis port 32. A large portion of time during a PCR assay is spent heating and cooling the reaction mix. To complete a PCR assay in a short period of time, rapid thermal cycling is critical. In order to accomplish this, analysis section 32 reduces the thermal mass of the heated PCR mixture and container, which allows temperature ramp rates as high as 30° C. per second. The equivalent advantage arises during cooling as well, with cooling rates of 5° C. per second achievable with test card 10 without active cooling.

In the illustrated embodiment, fluid microchannel 34 is also wider at target zone 66 than at the rest of microchannel 34. The wider portion of fluid microchannel 34 allows for more of the fluid sample to be present in target zone 66 during the assay. In an embodiment, first fluid detection zone 50 and second fluid detection zone 54 can also be made to be wider than the rest of microchannel 34. Alternatively, target zone 66 can be the same width as the rest of fluid microchannel 34.

Test card 10 also includes screen printed electrical contacts 68, which are in electrical communication with each of screen printing electrodes 56, 58 and 64 via electrical lines 70 (FIG. 8). By placing a current source in electrical contact with screen printed electrical contacts 68, the current source can activate capacitive sensor 60, capacitive sensor 62, and/or heating electrodes 64. As with electrodes 56, 58 and 64, electrical contacts 68 are printed on bottom substrate 12 with a conductive ink 40. In the illustrated embodiment, each of electrodes 56, 58 and 64, electrical contacts 68 and electrical lines 70 are printed with the same conductive ink 40.

Figure 15:
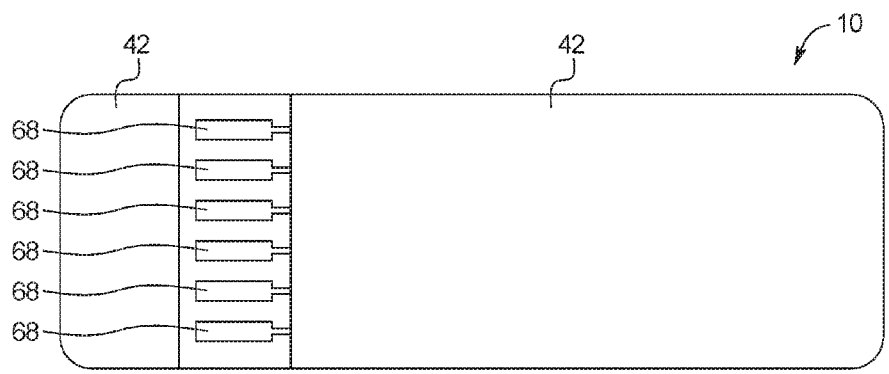
FIG. 15 is a bottom view of the test card of FIG. 1.

FIG. 15 shows a bottom view of a fully assembled test card 10. As illustrated, dielectric ink 42 has been printed over the majority of the electrical components formed by conductive ink 40. Dielectric ink 42 serves as protective, non-conductive coating to encapsulate the electrical components. The only electrical components visible from the bottom of test card 10 are electrical contacts 68 because electrical contacts 68 are the only electrical component that is intended to contact an outside source of current. By applying current from the outside source to electrical contacts 68, all other electrical components of test card 10 can be powered and controlled. As illustrated, electrical contacts 68 can be separated from each other (e.g., not be electrically connected to each other on test card 10) so that each of electrodes 56, 58 and 64 can be controlled independently of each other.

Figure 16A:
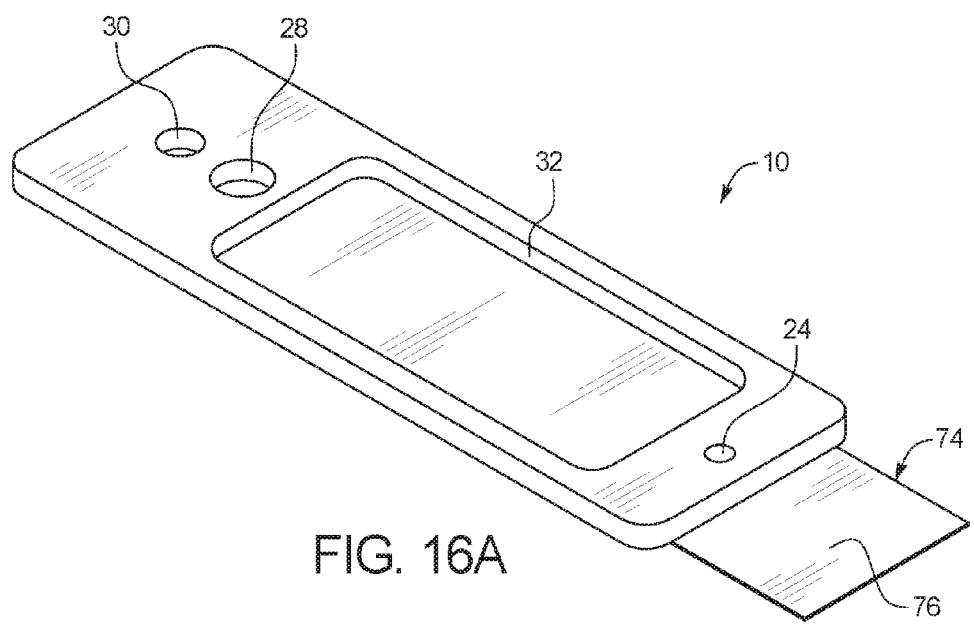
FIGS. 16A and 16B are top perspective views of the test card of FIG. 1 with a sealing layer.
Figure 16B:
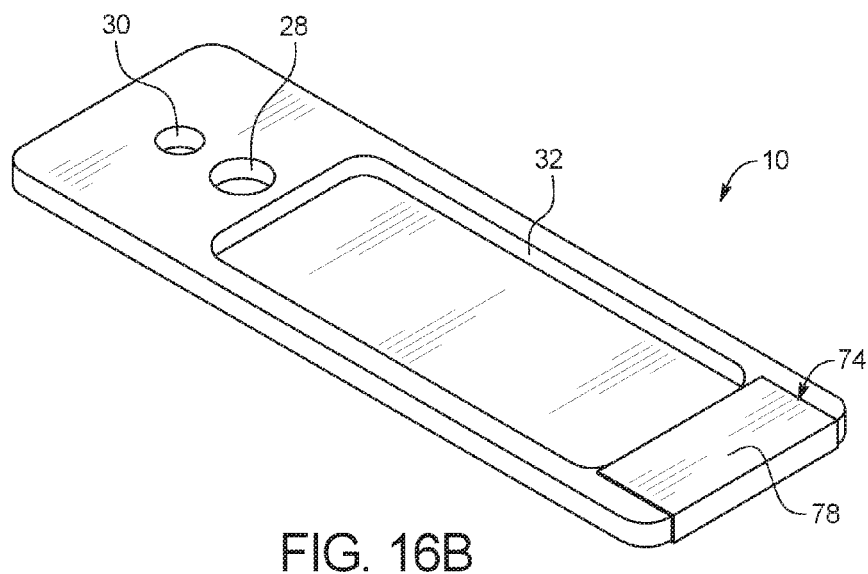

FIGS. 16A and 16B illustrate a fully assembled test card 10 with a sealing layer 74 attached. FIG. 16A shows test card 10 before a fluid sample has been added to inlet port 24, while FIG. 16B shows test card 10 after a fluid sample has been added to inlet port 24. In FIG. 16A, sealing layer 74 is attached to a bottom surface of test card 10, for example, by an adhesive on inner surface 76 of sealing layer 74. After a fluid sample is added to inlet port 24 of test card 10, sealing layer 74 is pulled over inlet port 24 as shown in FIG. 16B so that the inner surface 76 of sealing layer 74 adheres to the top surface of test card 10 and covers inlet port 24 to prevent any fluid from evaporating from inlet port 24. In FIG. 16B, the inner surface 76 of sealing layer 74 is pressed against the test card 10 and only the outer surface 78 of sealing layer 74 is exposed. Sealing layer 74 can be, for example, a peelable tape or membrane material with adhesive on inner surface 76. In an embodiment, sealing layer 74 is attached to the bottom surface of test card 10 prior to the introduction of the fluid sample into inlet port 24, and a disposable layer can be peeled back from the inner surface 76 of sealing layer 74 to expose adhesive on inner surface 76 to allow sealing layer 74 to adhere to test card 10 over inlet port 24. In another embodiment, sealing layer 74 can remain detached from test card 10 until after the fluid sample has been introduced into test card 10.

Figure 17:
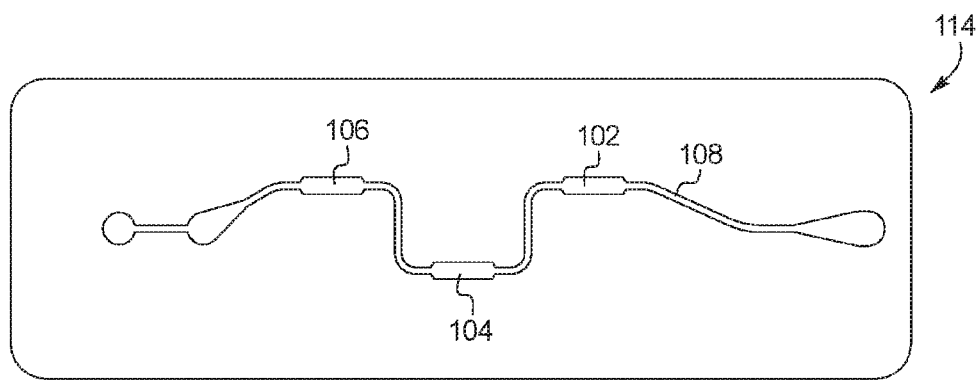
FIG. 17 is an example of an alternative embodiment of a channel layer that can be used with a test card according to the present disclosure.

FIG. 17 illustrates an alternative embodiment of a channel layer 114 of a test card 100 according to the present disclosure. Test card 100 is assembled the same way as test card 10, and differs only in the construction of channel layer 114 and a corresponding printed circuit layer 22. It will be understood by those of ordinary skill in the art that any of the features of test card 100 can be incorporated into test card 10, and vice versa.

As illustrated, test card 100 includes three separate target zones 102, 104, 106 along fluid microchannel 108. The printed circuit layer 22 can accordingly include three separate sets of electrodes (not shown) aligned with each of the target zones 102, 104, 106. By locating three separate target zones 102, 104, 106 along fluid microchannel 108, three assays on the same fluid sample can be performed and analyzed at the same time. In the illustrated embodiment, microchannel 108 curves through channel layer 114 to take advantage of the full width of test card 100 and provide distance between each of the target zones 102, 104, 106. Fluid detection zones can also be included along microchannel 108 as discussed above.

Figure 18:
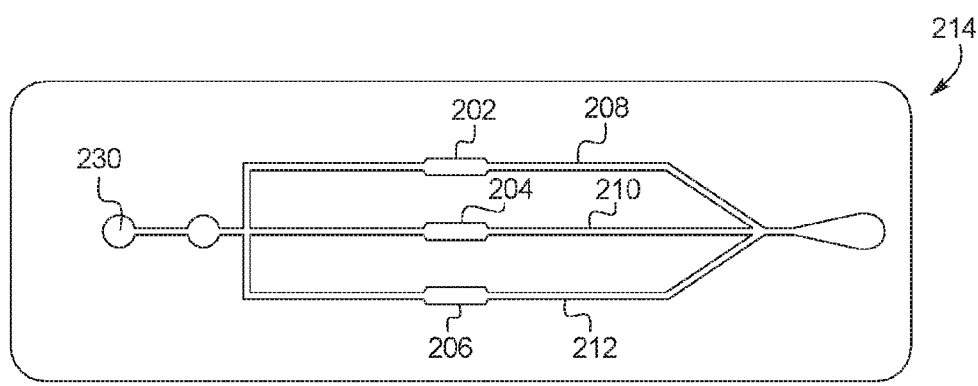
FIG. 18 is an example of an alternative embodiment of a channel layer that can be used with a test card according to the present disclosure.

FIG. 18 illustrates an alternative embodiment of a channel layer 214 of a test card 200 according to the present disclosure. Test card 200 is assembled the same way as test card 10, and differs only in the construction of channel layer 214 and a corresponding printed circuit layer 22. It will be understood by those of ordinary skill in the art that any of the features of test card 200 can be incorporated into test card 10 and/or test card 100, and vice versa.

As illustrated, test card 200 includes three separate target zones 202, 204, 206 along three separate fluid microchannels 208, 210, 212. The printed circuit layer 22 can accordingly include three separate sets of electrodes (not shown) aligned with each of the target zones 202, 204, 206. As a vacuum pressure is applied to outlet port 230, the pressure pulls a fluid sample through all three separate target zones 202, 204, 206, so that three assays on the same fluid sample can be performed and analyzed at the same time. Fluid detection zones can also be included along microchannels 208, 210, 212 as discussed above.

Figure 19:
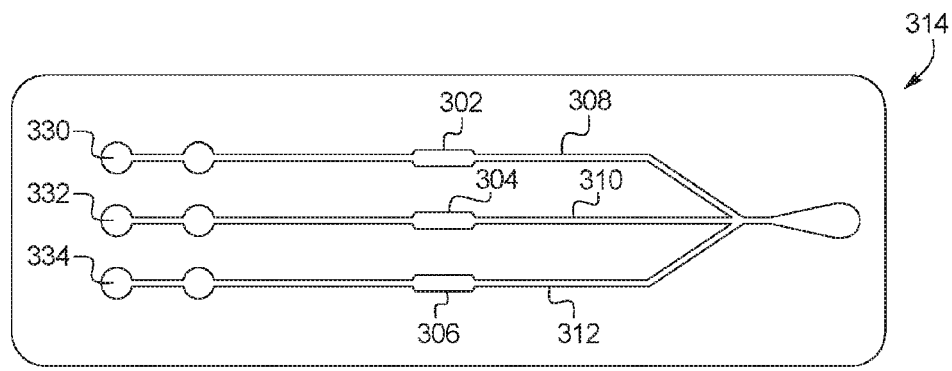
FIG. 19 is an example of an alternative embodiment of a channel layer that can be used with a test card according to the present disclosure.

FIG. 19 illustrates an alternative embodiment of a channel layer 314 of a test card 300 according to the present disclosure. Test card 300 is assembled the same way as test card 10, and differs only in the construction of channel layer 314 and a corresponding circuit layer. The middle substrate layer, adhesive layer and top substrate layer will also have their respective apertures realigned. It will be understood by those of ordinary skill in the art that any of the features of test card 300 can be incorporated into test card 10, test card 100 and/or test card 200, and vice versa.

As illustrated, test card 300 includes three separate target zones 302, 304, 306 along three separate fluid microchannels 308, 310, 312. The printed circuit layer can accordingly include three separate sets of electrodes (not shown) aligned with each of the target zones 302, 304, 306. Each of the separate fluid microchannels 308, 310, 312 is in fluid communication with a respective outlet port 330, 332, 334. In use, three separate vacuum sources can be attached to the three separate outlet ports 330, 332, 334, so that fluid from the fluid sample can be pulled into the three separate target zones 302, 304, 306 at different times. Fluid detection zones can also be included along microchannels 308, 310, 312 as discussed above.

Figure 20:
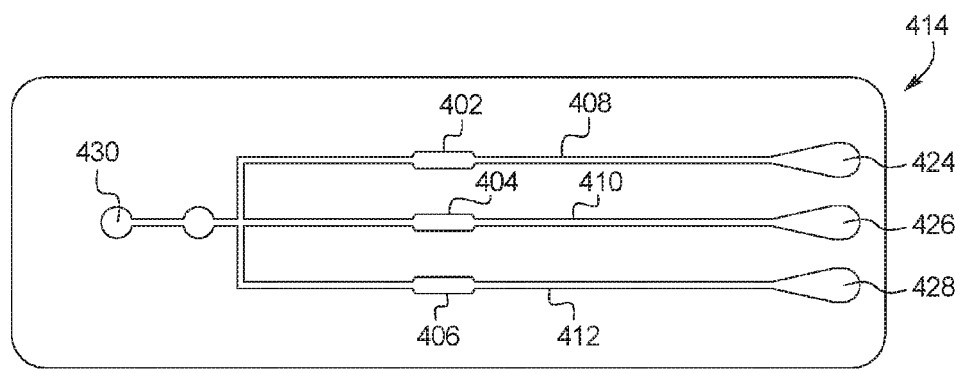
FIG. 20 is an example of an alternative embodiment of a channel layer that can be used with a test card according to the present disclosure.

FIG. 20 illustrates an alternative embodiment of a channel layer 414 of a test card 400 according to the present disclosure. Test card 400 is assembled the same way as test card 10, and differs only in the construction of channel layer 414 and a corresponding circuit layer. The middle substrate layer, adhesive layer and top substrate layer will also have their respective apertures realigned. It will be understood by those of ordinary skill in the art that any of the features of test card 400 can be incorporated into test card 10, test card 100, test card 200 and/or test card 300, and vice versa.

As illustrated, test card 400 includes three separate target zones 402, 404, 406 along three separate fluid microchannels 408, 410, 412. The printed circuit layer can accordingly include three separate sets of electrodes (not shown) aligned with each of the target zones 402, 404, 406. Each of the separate fluid microchannels 408, 410, 412 is in fluid communication with a respective inlet port 424, 426, 428, so that three separate fluid samples can be injected into test card 400 at the same time. In use, a single vacuum source can be attached to outlet ports 430, so that fluid from each of the fluid samples can be pulled into the three separate target zones 402, 404, 406 at the same time. Fluid detection zones can also be included along microchannels 408, 410, 412 as discussed above.

Figure 21:
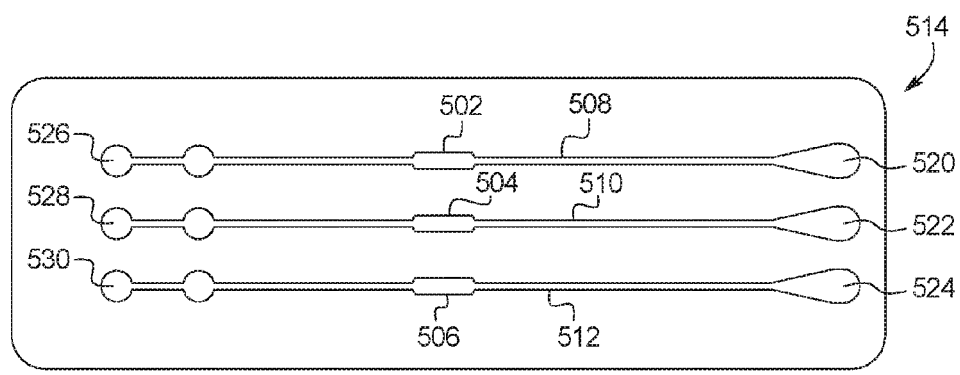
FIG. 21 is an example of an alternative embodiment of a channel layer that can be used with a test card according to the present disclosure.

FIG. 21 illustrates an alternative embodiment of a channel layer 514 of a test card 500 according to the present disclosure. Test card 500 is assembled the same way as test card 10, and differs only in the construction of channel layer 514 and a corresponding circuit layer. The middle substrate layer, adhesive layer and top substrate layer will also have their respective apertures realigned. It will be understood by those of ordinary skill in the art that any of the features of test card 500 can be incorporated into test card 10, test card 100, test card 200, test card 300 and/or test card 400, and vice versa.

As illustrated, test card 500 includes three separate target zones 502, 504, 506 along three separate fluid microchannels 508, 510, 512. The printed circuit layer can accordingly include three separate sets of electrodes (not shown) aligned with each of the target zones 502, 504, 506. Each of the separate fluid microchannels 508, 510, 512 is in fluid communication with a respective inlet port 520, 522, 524 and a respective outlet port 526, 528, 530. In use, three separate fluid samples can be injected into the inlet ports 520, 522, 524, and three separate vacuum sources can placed at the outlet ports 526, 528, 530, so that flow to each of the target zones 502, 204, 506 through each of the fluid microchannels 508, 510, 512 can be separately controlled. Fluid detection zones can also be included along microchannels 508, 510, 512 as discussed above.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A method of manufacturing a test card for analysing a fluid sample, comprising:

cutting at least a microchannel into a first polymer material to form a channel layer;
cutting a first aperture and a second aperture into a second polymer material to form a first substrate layer;
bonding the first substrate layer to a first side of the channel layer and a second substrate layer to a second side of the channel layer to form a single bonded layer with the microchannel passing therethrough and placing the first aperture and the second aperture in fluid communication with each other;
forming a third substrate layer to be thicker than the first substrate layer and the second substrate layer;
printing a conductive ink onto a first side of the bonded layer; and
adhering the third substrate layer to a second side of the bonded layer opposite the first side to form the test card, wherein the formed test card has a first surface formed by third substrate layer and an opposite second surface with the conductive ink exposed for contact with an outside source of current.

2. The method of claim 1, which includes diffusion bonding the first substrate layer to the first side of the channel layer and the second substrate layer to the second side of the channel layer.

3. The method of claim 1, which includes filling the microchannel with a surfactant solution.

4. The method of claim 1, which includes filling the microchannel with a surfactant solution including water and then allowing the water to evaporate to leave behind a layer of surfactant molecules on a surface of the microchannel.

5. The method of claim 1, which includes cutting a third aperture and a fourth aperture into the third substrate layer, and aligning the third aperture with the first aperture and the fourth aperture with the second aperture when adhering the third substrate layer to the bonded layer.

6. The method of claim 5, which includes cutting the third aperture to have two different cross-sectional areas, a first cross sectional area forming an inlet port on one side of the third substrate layer, and a second cross-sectional area forming at least part of a mixing chamber on an opposite side of the third substrate layer.

7. The method of claim 1, which includes cutting an analysis port aperture into the third substrate layer, and aligning the analysis port aperture with a target zone of the microchannel when adhering the third substrate layer to the bonded layer.

8. The method of claim 1, which includes printing a layer of dielectric ink over at least a portion of the conductive ink on the one first side of the bonded layer.

9. The method of claim 7, wherein the target zone is aligned with electrodes formed by the conductive ink, and wherein the electrodes are aligned within borders of the analysis port aperture when the test card is formed.

10. The method of claim 7, which includes aligning the analysis port aperture with both the target zone and a fluid detection zone of the microchannel when adhering the third substrate layer to the bonded layer.

11. The method of claim 10, wherein the fluid detection zone is a first fluid detection zone upstream of the target zone along the microchannel, and which includes aligning the analysis port aperture to further surround a second fluid detection zone downstream of the target zone along the microchannel.

12. The method of claim 1, which includes cutting an analysis port aperture into the third substrate layer, and aligning the analysis port aperture so that the first aperture aligns outside of borders of the analysis port aperture when the test card is formed.

13. The method of claim 1, which includes cutting an analysis port aperture into the third substrate layer, and aligning the analysis port aperture so that the second aperture aligns outside of borders of the analysis port aperture when the test card is formed.

14. The method of claim 1, which includes cutting an analysis port aperture into the third substrate layer, and aligning the analysis port aperture so that at least one electrical contact formed by the conductive ink and exposed for contact with the outside source of current aligns outside of borders of the analysis port aperture when the test card is formed.

15. The method of claim 1, which includes cutting an analysis port aperture into the third substrate layer, wherein a length of the analysis port aperture taken along a direction of the test card from the first aperture to the second aperture is more than half of a length of the third substrate layer in a same direction.

16. The method of claim 1, which includes cutting an analysis port aperture into the third substrate layer, wherein a width of the analysis port aperture taken approximately perpendicular to a direction of the test card from the first aperture to the second aperture is more than half of a width of the third substrate layer in a same direction.

17. The method of claim 1, wherein the conductive ink on the first side of the bonded layer is the only component of the test card intended to contact the outside source of current.

* * * * *